(12) United States Patent
Haque et al.

(10) Patent No.: US 12,416,047 B2
(45) Date of Patent: Sep. 16, 2025

(54) NONINVASIVE PRENATAL DIAGNOSTIC METHODS

(71) Applicant: Myriad Women's Health, Inc., South San Francisco, CA (US)

(72) Inventors: Imran Saeedul Haque, San Francisco, CA (US); Jared Robert Maguire, Oakland, CA (US); Clement Chu, South San Francisco, CA (US); Eric Andrew Evans, Brisbane, CA (US)

(73) Assignee: Myriad Women's Health, Inc., South San Francisco, CA (US)

( * ) Notice: Subject to any disclaimer, the term of this patent is extended or adjusted under 35 U.S.C. 154(b) by 1366 days.

(21) Appl. No.: 15/587,811

(22) Filed: May 5, 2017

(65) Prior Publication Data

US 2017/0321270 A1    Nov. 9, 2017

Related U.S. Application Data

(60) Provisional application No. 62/333,087, filed on May 6, 2016.

(51) Int. Cl.
| | | |
|---|---|---|
| C12Q 1/68 | (2018.01) | |
| C12Q 1/6874 | (2018.01) | |
| C12Q 1/6881 | (2018.01) | |

(52) U.S. Cl.
CPC ......... *C12Q 1/6874* (2013.01); *C12Q 1/6881* (2013.01); *C12Q 2600/156* (2013.01); *C12Q 2600/172* (2013.01)

(58) Field of Classification Search
CPC .... C12Q 1/686; C12Q 1/6874; C12Q 1/6883; C12Q 1/6827; C12Q 2600/156; C12Q 2600/172; C12Q 1/6806; C12Q 2525/161; C12Q 2535/122; C12Q 2537/159; C12Q 2563/179; C12Q 2565/514; C12N 15/10; C12N 15/1003; C12N 15/1093; G06F 19/18; G06F 19/22; C40B 20/00; C40B 20/04

See application file for complete search history.

(56) References Cited

U.S. PATENT DOCUMENTS

| | | | |
|---|---|---|---|
| 8,383,338 B2 | 2/2013 | Kitzman | |
| 9,092,401 B2 | 7/2015 | Richards | |
| 9,309,556 B2 | 4/2016 | Myllykangas | |
| 2012/0184449 A1* | 7/2012 | Hixson et al. ......... | C40B 30/00 506/7 |
| 2012/0196754 A1* | 8/2012 | Quake ................. | C12Q 1/6881 435/287.2 |
| 2012/0208705 A1 | 8/2012 | Steemers | |
| 2013/0225452 A1 | 8/2013 | Pollack | |
| 2013/0253844 A1* | 9/2013 | Lo ......................... | G16B 20/00 702/19 |
| 2013/0261019 A1 | 10/2013 | Lin | |
| 2013/0288254 A1* | 10/2013 | Pollack et al. ........ | C12Q 1/686 |
| 2014/0024541 A1 | 1/2014 | Richards | |
| 2014/0162278 A1 | 6/2014 | Richards | |
| 2014/0342354 A1* | 11/2014 | Evans et al. ......... | C12Q 1/6827 435/6.11 |
| 2015/0080266 A1 | 3/2015 | Volkmuth | |
| 2015/0205914 A1 | 7/2015 | Richards | |
| 2015/0211070 A1* | 7/2015 | Seligson .............. | A61K 31/713 506/3 |
| 2015/0376700 A1* | 12/2015 | Schnall-Levin ....... | G16B 30/20 506/4 |
| 2017/0355984 A1 | 12/2017 | Evans | |
| 2018/0089364 A1 | 3/2018 | Muzzey | |
| 2018/0127809 A1* | 5/2018 | Andruzzi et al. .... | C12Q 1/6806 |
| 2018/0148781 A1* | 5/2018 | Andruzzi et al. .... | C12Q 1/6874 |

FOREIGN PATENT DOCUMENTS

| | | | | |
|---|---|---|---|---|
| WO | 2012003374 | | 1/2012 | |
| WO | 2012040387 | | 3/2012 | |
| WO | 2013112923 | | 8/2013 | |
| WO | WO-2016011414 A1 * | | 1/2016 | ........... C12Q 1/6827 |
| WO | WO-2016040901 A1 * | | 3/2016 | ......... C12N 15/1065 |

OTHER PUBLICATIONS

"Noninvasive prenatal testing for autosomal recessive conditions by maternal plasma sequencing in a case of congenital deafness" Genetics in Medicine 16:972-976 (2014), doi:10.1038/gim.2014.51 (Year: 2014).*
Belkadi et al. "Comparison of WGS and WES to detect exome variants" Proc. Nat. Acad. Sci. Apr. 2015, 112 (17) 5473-5478, DOI: 10.1073/pnas.1418631112 with 7 sheets of Suppl. Information from Belkadi et al. 10.1073/pnas.1418631112. (Year: 2015).*
Bowen "Haemophilia A and haemophilia B: molecular insights." Mol Pathol. 2002; 55(1):1-18. doi:10.1136/mp.55.1.1) (Year: 2002).*
Alex et al. "Differences in allele frequencies of autosomal dominant hypercholesterolemia SNPs in the Malaysian population" J Hum Genet 57, 358-362 (2012); https://doi.org/10.1038/jhg.2012.34 (Year: 2012).*
Steiner et al. "The role of common single-nucleotide polymorphisms on exon 9 and exon 12 skipping in nonmutated CFTR alleles" Hum Mutat. Aug. 2004;24(2):120-9; doi: 10.1002/humu.20064 (Year: 2004).*

(Continued)

*Primary Examiner* — Sahana S Kaup
(74) *Attorney, Agent, or Firm* — Foley & Lardner LLP

(57) ABSTRACT

Prenatal genetic testing allows early detection of genetic disease in a fetus. Described herein are methods of detecting the presence or absence of a genetic variant in a region of interest in the genome of a fetus in a pregnant woman. The methods are noninvasive, and can use cell-free DNA (cfDNA) present in the plasma of the pregnant woman. A DNA library is constructed from the cfDNA, and DNA molecules comprising the region of interest or portions thereof are enriched and analyzed, for example by sequencing. The methods described herein can also rely on constructing a maternal haplotype to provide even higher resolution fetal genetic variant determination.

31 Claims, 6 Drawing Sheets

(56) References Cited

OTHER PUBLICATIONS

Li et al. "A comprehensive database of Duchenne and Becker muscular dystrophy patients (0-18 years old) in East China" Orphanet J Rare Dis 10, 5 (2015). https://doi.org/10.1186/s13023-014-0220-7 (Year: 2015).*

Amarasinghe et al. "Opportunities and challenges in long-read sequencing data analysis" Genome Biol 21, 30 (2020). https://doi.org/10.1186/s13059-020-1935-5 (Year: 2020).*

Debrand et al.( "A non-invasive droplet digital PCR (ddPCR) assay to detect paternal CFTR mutations in the cell-free fetal DNA (cffDNA) of three pregnancies at risk of cystic fibrosis via compound heterozygosity." PloS one 10.11 (2015): e0142729.) . (Year: 2015).*

Branton, D et al. (Oct. 2008). "The Potential and Challenges of Nanopore Sequencing," Nat. Biotechnol. 26(10):1146-1153, seventeen pages.

Browning, S.R. et al. (Sep. 16, 2011). "Haplotype Phasing: Existing Methods and New Developments," Nat Rev Genet 12(10):703-714, twenty six pages.

Edlow, AG et al., "Tracking fetal development through molecular analysis of maternal biofluids", Biochimica et Biophysica Acta (BBA)—Molecular Basis of Disease, (20121200), vol. 1822, No. 12, pp. 1970-1980, XP055439781.

Fan, H.C. et al. (Jul. 19, 2012; e-published on Jul. 4, 2012). "Non-Invasive Prenatal Measurement of Fetal Genome," Nature 487:320-324, eight pages (Including Supplementary material).

Fierer, N. et al. (Nov. 18, 2008). "The Influence of Sex, Handedness, and Washing on the Diversity of Hand Surface Bacteria," Proc. Nat'l Adad. Sci. 105(46):17994-17999.

Hamady, M. et al. (Mar. 2008; e-published on Feb. 10, 2008). "Error-Correcting Barcoded Primers Allow Hundreds of Samples to by Pyrosequenced In Multiplex," Nature Methods 5(3):235-237, six pages.

Hopmans, E.S. et al. (Apr. 29, 2014). "A Programmable Method For Massively Parallel Targeted Sequencing," Nucleic Acids Res. 42(10):e88, pp. 1-16.

Huseman, A. (Jan. 4, 2017). "Bayer Genetics Launches PreSeekTM—1st Non-Invasive Prenatal Multi-Gene Sequencing Screen," Bayer College of Medicine, located at <https://www.bcm.edu/news/genetics/baylor-genetics-prenatal-sequencing>.

Illumina. (Jul. 17, 2013). "Phasing Analysis Service for Whole Human Genome Sequencing-Delivering Whole-Genome Phase Information for a Comprehensive View of Genomic Complexity," Illumina Publication No. 770-2013-026, two pages.

Illumina. (Nov. 19, 2014). "Phasing Analysis Service for Human WGS-Illumina Genome Network Delivers Comprehensive View of Human Genomic Complexity," Illumina Publication No. 770-2013-024, four pages.

Karamitros, T et al. , "A novel method for the multiplexed target enrichment of MinION next generation sequencing libraries using PCR-generated baits", Nucleic Acids Research, (Dec. 15, 2015), vol. 43, No. 22, p. e152, XP055439778.

Kitzman, J.O. et al. (Jan. 2011; e-published on Dec. 19, 2010). "Haplotype-Resolved Genome Sequencing of a Gujarati Indian Individual," Nature Biotechnology 29(1):59-63.

Kitzman, J.O. et al. (Jun. 6, 2012). "Noninvasive Whole-Genome Sequencing of a Human Fetus," Science Translation Medicine 4(137):137RA76, pp. 1-8, total nineteen pages, (Including Supplementary material).

Koren, S. et al. (Feb. 2015; e-published on Dec. 1, 2014). "One Chromosome, One Contig: Complete Microbial Genomes From Long-Read Sequencing and Assembly," Curr. Opin. Microbial. 23:110-120.

Krishnan, A.R. et al. (Feb. 17, 2011). "Barcodes for DNA Sequencing With Guaranteed Error Correction and Capability," Electronics Letters 47(4):236-237.

Lanman, R.B. et al. (Oct. 16, 2015). "Analytical and Clinical Validation of a Digital Sequencing Panel for Quantitative, Highly Accurate Evaluation of Cell-Free Circulating Tumor DNA," PLoS One 10:e0140712, pp. 1-27.

Lefrançois, P. et al. (Jan. 21, 2009). "Efficient Yeast Chip-Seq Using Multiplex Short-Read DNA Sequencing," BMC Genomics 10:1-18.

Lun, F.M.F. et al. (Dec. 16, 2008). "Noninvasive Prenatal Diagnosis of Monogenic Diseases by Digital Size Selection and Relative Mutation Dosage on DNA in Maternal Plasma," Proceedings of the National Academy of Sciences of the U.S.A. 105(50):19920-19925.

Mazloom, AR et al., "Noninvasive prenatal detection of sex chromosomal aneuploidies by sequencing circulating cell-free DNA from maternal plasma", Prenatal Diagnosis, (20130600), vol. 33, No. 6, pp. 591-597, XP055089609.

Mertes, F. et al. (Nov. 2011; e-published on Nov. 26, 2011). "Targeted Enrichment of Genomic DNA Regions for Next-Generation Sequencing," Briefings in Functional Genomics 10(6):374-386.

Myllykangas, S. et al. (Nov. 2011; e-published on Oct. 23, 2011). "Efficient Targeted Resequencing of Human Germline and Cancer Genomes by Oligonucleotide-Selective Sequencing," Nat Biotechnol. 29(11):1024-1027.

Ng, S.B. et al. (Sep. 10, 2009; e-published on Aug. 16, 2009). "Targeted Capture and Massively Parallel Sequencing of Twelve Human Exomes," Nature 461(7261):272-276.

\* cited by examiner

NONINVASIVE PRENATAL DIAGNOSTIC METHODS

CROSS-REFERENCE TO RELATED APPLICATION

This application claims priority to U.S. Provisional Application No. 62/333,087, filed on May 6, 2016, entitled "NONINVASIVE PRENATAL DIAGNOSIS," which is incorporated herein by reference for all purposes.

FIELD OF THE INVENTION

The present invention relates to methods of detecting genetic variants in a fetus.

BACKGROUND

Prenatal genetic testing allows early detection of genetic disease in a fetus. Many fetal genetic disorders arise from large chromosomal defects, such as aneuploidy. Other disorders can be a result of inherited or de novo mutations, such as single nucleotide variants, multiple nucleotide variants, insertion or deletion variants ("indel" variants), or copy number variants. During pregnancy, many soon-to-be parents or physicians want to understand the risk of such disorders in an unborn fetus to prepare for any undesirable diagnosis.

Previously known methods of prenatal testing included invasive sampling by amniocentesis or chorionic villus sampling. Samples obtained using these methods can by analyzed for certain chromosomal abnormalities, such as whether the whether the offspring will have Down syndrome, trisomy 13, or trisomy 18. However, such invasive methods posed significant risks to the fetus.

The discovery that fetal cell-free DNA (cfDNA) is present in the mother's plasma has allowed for noninvasive prenatal testing. Only about 4-13% of the cfDNA in the mother's plasma is attributable to the fetal genome, with the remainder being from the mother herself. Thus, whole genome sequencing of a cfDNA sample does not adequately distinguish fetal cfDNA from maternal cfDNA. While haplotype resolution provides some increased sensitivity (see, e.g., Kitzman et al., *Noninvasive Whole-Genome Sequencing of a Human Fetus*, Sci. Trnasl. Med., vol. 4 (including supplemental material) (2012); Fan et al., *Non-invasive prenatal measurement of the fetal genome*, Nature, vol. 487, pp. 320-324 (and supplemental material) (2012)), such methods fail to provide resolution with sufficient accuracy for adequate fetal genetic variant determination.

SUMMARY OF THE INVENTION

Provided herein there is a method of detecting the presence or absence of a genetic variant in a region of interest in the genome of a fetus in a pregnant woman, comprising (a) obtaining cell-free DNA from a plasma sample of the pregnant woman; (b) preparing a DNA library from said cell-free DNA, the DNA library comprising a population of DNA molecules; (c) preferentially analyzing the population of DNA molecules from said DNA library, wherein the DNA molecules comprising a portion of the region of interest are enriched; (d) detecting the presence or absence of the fetal genetic variant based on the cell-free DNA sequencing reads. In some embodiments, the DNA molecules comprise a barcode. In some embodiments, analyzing comprises preferentially sequencing the DNA molecules comprising the portion of the region of interest. In some embodiments, analyzing comprises sequencing the enriched DNA molecules to produce a plurality of cell-free DNA sequencing reads. In some embodiments, analyzing comprises first enriching the DNA molecules comprising the portion of the region of interest, and second sequencing the DNA molecules comprising the portion of the region of interest. In some embodiments, analyzing comprises subjecting the enriched DNA molecules to digital PCR produce a plurality of cell-free DNA sequencing reads.

Further, there is provided herein a method of detecting the presence or absence of a genetic variant in a region of interest in the genome of a fetus in a pregnant woman, comprising (a) obtaining cell-free DNA from a plasma sample of the pregnant woman; (b) preparing a DNA library from said cell-free DNA, wherein the DNA library comprises a plurality of DNA molecules comprising molecular barcodes; (c) obtaining an enriched population of DNA molecules from said DNA library, wherein the enriched population of DNA molecules comprise the region of interest; (d) sequencing the enriched DNA molecules to produce a plurality of cell-free DNA sequencing reads; and (e) detecting the presence or absence of the fetal genetic variant based on the cell-free DNA sequencing reads. In some embodiments, the method further comprises incorporating the molecular barcode in the DNA molecules.

Also provided herein is a method of detecting the presence or absence of a genetic variant in a region of interest in the genome of a fetus in a pregnant woman, comprising (a) obtaining an enriched population of DNA molecules from a DNA library comprising a plurality of DNA molecules comprising molecular barcodes, wherein the DNA library is prepared from cell-free DNA in a plasma sample of the pregnant woman, and wherein the enriched population of DNA molecules comprise the region of interest; (b) sequencing the enriched DNA molecules to produce a plurality of cell-free DNA sequencing reads; and detecting the presence or absence of the fetal genetic variant based on the cell-free DNA sequencing reads. In some embodiments, the method further comprises incorporating the molecular barcode in the DNA molecules. In some embodiments, the molecular barcodes are incorporated into the DNA molecules and the DNA molecules are enriched simultaneously.

Additionally, there is provided herein a method of detecting the presence or absence of a genetic variant in a region of interest in the genome of a fetus in a pregnant woman, comprising (a) obtaining cell-free DNA from a plasma sample of the pregnant woman; (b) preparing a DNA library from said cell-free DNA, wherein the DNA library comprises a plurality of DNA molecules comprising molecular barcodes; (c) sequencing a portion of the DNA library to produce a plurality of cell-free DNA sequencing reads, wherein the portion of the DNA library is enriched for DNA molecules comprising the region of interest; and (d) detecting the presence or absence of the fetal genetic variant based on the cell-free DNA sequencing reads. In some embodiments, the method further comprises incorporating the molecular barcode in the DNA molecules. In some embodiments, the molecular barcodes are incorporated into the DNA molecules and the DNA molecules are enriched simultaneously.

In some embodiments of the methods described above, the molecular barcodes are incorporated into the DNA molecules prior to enrichment.

In some embodiments, the enrichment is carried out by PCR amplification. In some embodiments, the enrichment is carried out by hybridization.

In some embodiments, the method detects the presence of a fetal genetic variant. In some embodiments, the method detects the absence of a fetal genetic variant.

In some embodiments, the method further comprises sequencing the corresponding region of interest in the genome of the pregnant woman to produce a plurality of maternal sequencing reads. In some embodiments, the corresponding region of interest in the genome of the pregnant woman is sequenced from DNA present in a maternal buffy coat. In some embodiments, the method further comprises constructing a maternal haplotype. In some embodiments, constructing the maternal haplotype comprises phasing genetic variants present in the maternal sequencing reads. In some embodiments, constructing the maternal haplotype comprises sequencing a corresponding region of interest in a biological relative of the pregnant woman. In some embodiments, constructing the maternal haplotype comprises statistical mapping. In some embodiments, the method further comprises enriching the corresponding region of interest in the genome of the pregnant woman. In some embodiments, detecting the presence or absence of the fetal genetic variant comprises computing a maternal allele frequency for the maternal sequencing reads; computing a cell-free DNA allele frequency for the cell-free DNA sequencing reads; and comparing the maternal allele frequency to the cell-free DNA allele frequency.

In some embodiments, the method further comprises sequencing the corresponding region of interest in a paternal genome to produce a plurality of paternal sequencing reads. In some embodiments, the method further comprises constructing a paternal haplotype. In some embodiments, constructing the paternal haplotype comprises phasing genetic variants present in the paternal sequencing reads.

In some embodiments, the fetal genetic variant is a single nucleotide polymorphism present in the fetus. In some embodiments, the fetal genetic variant is a single-nucleotide variant, a multi-nucleotide variant, or an indel variant of about 100 bp or less. In some embodiments, detecting the presence or absence of the fetal genetic variant comprises using the molecular barcode to distinguish the single nucleotide polymorphism variant from random or systematic errors.

In some embodiments, the fetal genetic variant is a copy number loss variant. In some embodiments, the fetal genetic variant is a DNA deletion variant. In some embodiments, detection comprises copy number counting. In some embodiments, the copy number counting comprises using the molecular barcode to filter out redundantly counted DNA sequences.

In some embodiments, the fetal genetic variant is a de novo variant. In some embodiments, the fetal genetic variant is an inherited variant. In some embodiments, the fetal genetic variant is maternally inherited. In some embodiments, the fetal genetic variant is paternally inherited. In some embodiments, the fetal genetic variant is an autosomal dominant variant. In some embodiments, the fetal genetic variant is an autosomal recessive variant.

DETAILED DESCRIPTION

Figure 1:
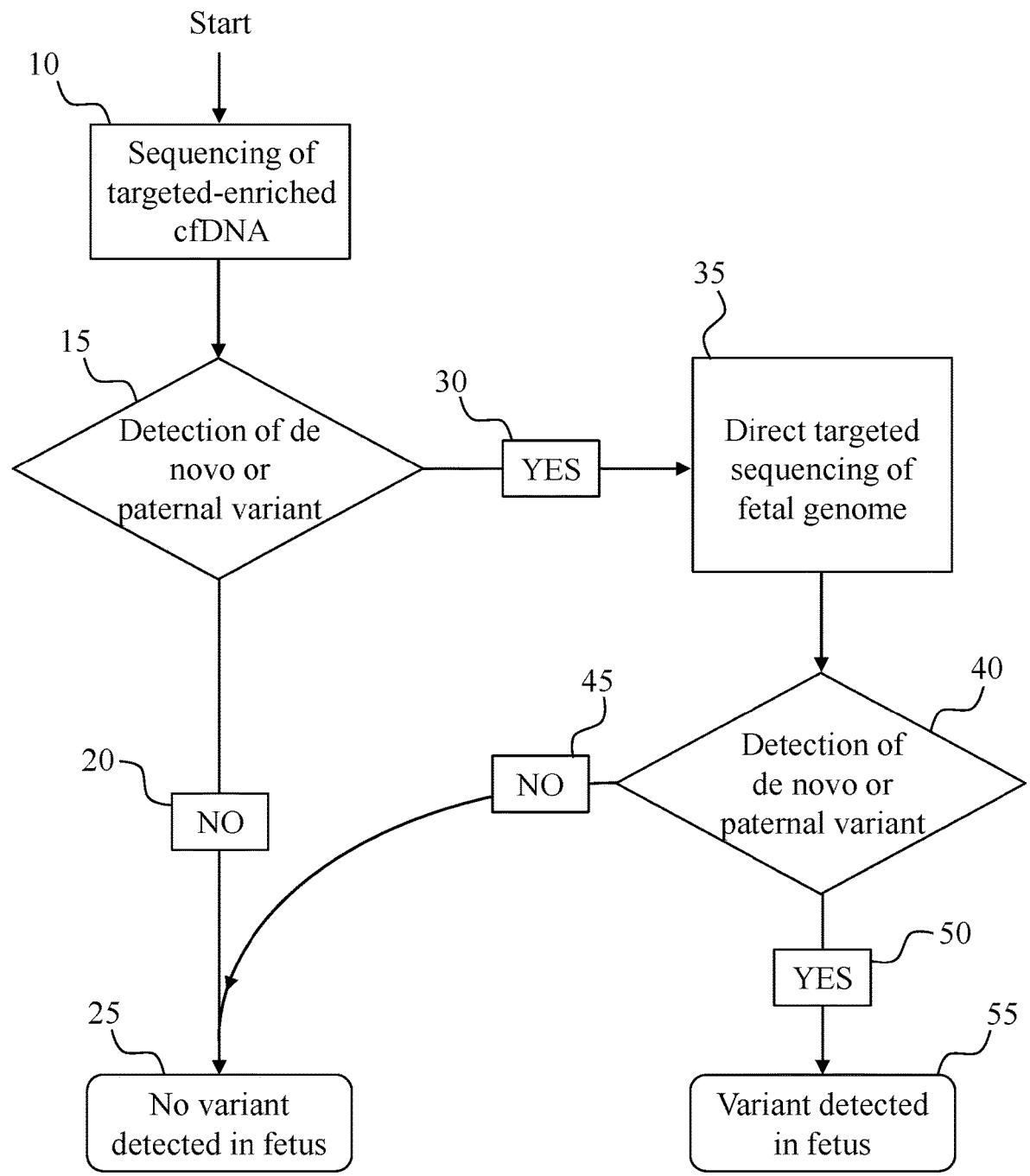
FIG. 1 is a schematic of one embodiment of a method for detecting, and optionally verifying, the presence or absence of a paternally-inherited dominant or de novo fetal genetic variant.

Provided herein are methods for detecting the presence or absence of a genetic variant in a region of interest in the genome of a fetus in a pregnant woman, comprising obtaining an enriched population of DNA molecules from a DNA library comprising a plurality of DNA molecules comprising molecular barcodes, wherein the DNA library is prepared from cell-free DNA (cfDNA) in a plasma sample of the pregnant woman, and wherein the enriched population of DNA molecules comprise the region of interest; sequencing the enriched DNA molecules to produce a plurality of cell-free DNA sequencing reads; and detecting the presence or absence of the fetal genetic variant based on the cell-free DNA sequencing reads. In some embodiments, the method comprises obtaining the cell-free DNA from a plasma sample of the pregnant woman. In some embodiments, the method comprises preparing a DNA library from the cell-free DNA, wherein the DNA library comprises a plurality of DNA molecules comprising molecular barcodes.

In some embodiments, the methods described herein further comprise constructing a maternal haplotype, for example by phasing genetic variants present in a predetermined sequenced region of the maternal genome, comparing the sequenced region of the maternal genome to a corresponding sequenced region of a biological relative, or by statistical mapping.

In some embodiments, there is provided a method for detecting the presence or absence of a genetic variant in a region of interest in the genome of a fetus in a pregnant woman, wherein the genetic variant is an autosomal dominant genetic variant (which can be, for example, a de novo variant or a paternally-inherited variant). In some embodiments, the autosomal dominant genetic variant is a disease-causing variant. In some embodiments, cell-free DNA is extracted from the maternal plasma of a pregnant woman. In some embodiments, a DNA library comprising a plurality of DNA molecules is prepared form the cell-free DNA. In some embodiments, the DNA molecules in the plurality of DNA molecules comprise an incorporated oligonucleotide, which can comprise a molecular barcode. DNA molecules comprising the region of interest or a portion of the region of interest are enriched, for example by hybrid capture. The enriched DNA molecules are then analyzed, for example by sequencing or digital PCR. Optionally, a maternal haplotype is constructed. The presence or absence of the fetal genetic variant based on the sequencing reads of the cell-free DNA is then detected, for example based on the presence or absence of a relative increase or decrease in allele frequency in the cell-free DNA. If a maternal haplotype is constructed, the allele frequency of the cell-free DNA can be compared to or attributed to the maternal haplotype.

In some embodiments, there is provided a method of detecting the presence or absence of a genetic variant in a region of interest in the genome of a fetus in a pregnant woman, wherein the genetic variant is an X-linked recessive variant (which can be, for example, a de novo variant or a paternally-inherited variant). In some embodiments, the X-linked recessive variant is a disease-causing variant. In some embodiments, cell-free DNA is extracted from the maternal plasma of a pregnant woman. In some embodiments, a DNA library comprising a plurality of DNA molecules is prepared form the cell-free DNA. In some embodiments, the DNA molecules in the plurality of DNA molecules comprise an incorporated oligonucleotide, which can comprise a molecular barcode. DNA molecules comprising the region of interest or a portion of the region of interest are enriched, for example by hybrid capture. The enriched DNA molecules are then analyzed, for example by sequencing or digital PCR. Optionally, a maternal haplotype is constructed. The presence or absence of the fetal genetic variant based on the sequencing reads of the cell-free DNA is then detected, for example based on the presence or absence of a relative increase or decrease in allele frequency in the cell-free DNA. If a maternal haplotype is constructed, the allele frequency of the cell-free DNA can be compared to or attributed to the maternal haplotype.

In some embodiments, there is provided a method of detecting the presence or absence of a genetic variant in a region of interest in the genome of a fetus in a pregnant woman, wherein the genetic variant is a copy number variant. In some embodiments, there is provided a method of detecting the presence or absence of a genetic variant in a region of interest in the genome of a fetus in a pregnant woman, wherein the genetic variant is a copy number loss variant. In some embodiments, the copy number loss variant is a microdeletion. In some embodiments, there is provided a method of detecting the presence or absence of a genetic variant in a plurality of regions of interest in the genome of a fetus in a pregnant woman, wherein the genetic variant is a copy number variant. In some embodiments, there is provided a method of detecting the presence or absence of a genetic variant in a plurality of regions of interest in the genome of a fetus in a pregnant woman, wherein the genetic variant is a copy number loss variant. In some embodiments, the copy number loss variant is a microdeletion. In some embodiments, cell-free DNA is extracted from the maternal plasma of a pregnant woman. In some embodiments, a DNA library comprising a plurality of DNA molecules is prepared form the cell-free DNA. In some embodiments, the DNA molecules in the plurality of DNA molecules comprise an incorporated oligonucleotide, which can comprise a molecular barcode. DNA molecules comprising the region of interest or a portion of the region of interest are enriched, for example by hybrid capture. The enriched DNA molecules are then analyzed, for example by sequencing or digital PCR. Optionally, a maternal haplotype is constructed. The presence or absence of the fetal genetic variant based on the sequencing reads of the cell-free DNA is then detected, for example based on the presence or absence of a relative increase or decrease in allele frequency in the cell-free DNA. If a maternal haplotype is constructed, the allele frequency of the cell-free DNA can be compared to or attributed to the maternal haplotype.

In some embodiments, there is provided a method for detecting the presence or absence of a genetic variant in a region of interest in the genome of a fetus in a pregnant woman, wherein the genetic variant is an autosomal recessive genetic variant. In some embodiments, cell-free DNA is extracted from the maternal plasma of a pregnant woman. In some embodiments, a DNA library comprising a plurality of DNA molecules is prepared form the cell-free DNA. In some embodiments, the DNA molecules in the plurality of DNA molecules comprise an incorporated oligonucleotide, which can comprise a molecular barcode. DNA molecules comprising the region of interest or a portion of the region of interest are enriched, for example by hybrid capture. The enriched DNA molecules are then analyzed, for example by sequencing or digital PCR. Optionally, a maternal haplotype is constructed. The presence or absence of the fetal genetic variant based on the sequencing reads of the cell-free DNA is then detected, for example based on the presence or absence of a relative increase or decrease in allele frequency in the cell-free DNA. If a maternal haplotype is constructed, the allele frequency of the cell-free DNA can be compared to or attributed to the maternal haplotype.

In some embodiments, the fetal genetic variant is verified. For example, in some embodiments, the fetal genetic variant is verified using an invasive technique, such as amniocentesis, chorionic villus sampling, or percutaneous umbilical cord blood sampling.

In some embodiments, the maternal genome and/or the paternal genome, or a portion thereof, is sequenced. In some embodiments, the sequenced portion of the maternal genome and/or paternal genome corresponds to a region of interest in the fetal genome. In some embodiments, this sequencing is performed to determine the carrier status of the mother or father. In some embodiments, the sequencing can be used to determine whether a given genetic sequence variant is an inherited variant or a de novo variant.

The methods described herein allow for a high-resolution determination of fetal genetic variants, such as inherited or de novo genetic variants such as small nucleotide polymorphism variants and copy number variants (such as copy number loss variants), using noninvasive techniques. The methods described herein use cell-free DNA circulating in a pregnant woman's plasma to detect the fetal genetic variant. Plasma of a pregnant woman contains not only her own cell-free DNA, but also cell-free DNA of the fetus. Depending on the length of pregnancy, the percentage of cell-free DNA originating from the fetus is generally thought range from about 4% to about 13%. Previous noninvasive methods could extract some genetic variant information from the cell-free DNA, but such information was of low resolution. The methods described herein provide higher resolution fetal genetic variant determination to allow for a more accurate diagnosis.

Because the amount of fetal cfDNA is relatively small compared to the maternal DNA, signal due to a fetal genetic sequence variant is often lost in the noise caused by signal due to the maternal genome. By enrichment of a particular region of interest, however, the signal to noise ratio of the fetal cfDNA can be substantially increased. Additionally, the incorporation of molecular barcodes in the cfDNA can be used to filter noise arising from spontaneous mutations during genetic amplification (particularly for the identification of small nucleotide polymorphism variants) or an imbalance in amplification rates in within particular genetic segments (particularly for CNV variants).

Genetic variants in a fetus can be inherited from a maternal or a paternal chromosome. The fetal genetic variants can also occur de novo by spontaneous mutagenesis. In some embodiments, the methods described herein are used to detect inherited variants, such as inherited dominant autosomal variants, inherited dominant autosomal variants, or inherited X-linked recessive variants. In some embodiments, the methods described herein are used to detect de novo mutations, such as de novo dominant autosomal variants, de novo recessive autosomal variants, or de novo X-linked variants. Any of these de novo or inherited mutations can be [SNP] small nucleotide polymorphism variants (including single nucleotide variants, multi-nucleotide variants, or indel variants) or copy number variants (including a genetic insertion or deletion). These mutations pose a risk of disease to the fetus, and parents and physicians are often interested in understanding the risk such variants pose to the fetus. By obtaining high-resolution identification of the fetal genetic variants, risks to the fetus can be assessed. The methods described herein provide such high-resolution fetal genetic variant determination.

Definitions

As used herein, the singular forms "a," "an," and "the" include the plural reference unless the context clearly dictates otherwise.

Reference to "about" a value or parameter herein includes (and describes) variations that are directed to that value or parameter per se. For example, description referring to "about X" includes description of "X".

The term "copy number variant" or "CNV" refers to any duplication or deletion of a genomic segment. A "copy number loss variant" or "CNLV" refers to a deletion of a genomic segment of more than about 100 base pairs.

The term "indel variant" refers to an insertion or a deletion variant.

The term "microdeletion" refers to a deletion of about 2 million base pairs to about 7 million base pairs.

The term "random or systematic error" means an artificially introduced sequence artifact.

The term "small nucleotide polymorphism" refers to a single-nucleotide variant (SNV), a multi-nucleotide variant (MNV), or an indel variant about 100 base pairs or less.

It is understood that aspects and variations of the invention described herein include "consisting" and/or "consisting essentially of" aspects and variations.

It is to be understood that one, some or all of the properties of the various embodiments described herein may be combined to form other embodiments of the present invention.

The disclosures of all publications, patents, and patent applications referred to herein are hereby incorporated herein by reference in their entireties.

Methods of Determining Fetal Genetic Variants

Provided herein is a method of detecting the presence or absence of a genetic variant in a region of interest in the genome of a fetus in a pregnant woman, comprising obtaining cell-free DNA from a plasma sample of the pregnant woman; preparing a DNA library from said cell-free DNA, the DNA library comprising a population of DNA molecules; preferentially analyzing the population of DNA molecules from said DNA library, wherein the DNA molecules comprising a portion of the region of interest are enriched; and detecting the presence or absence of the fetal genetic variant based on the cell-free DNA sequencing reads. In some embodiments, the DNA molecules comprise a barcode. In some embodiments, analyzing comprises preferentially sequencing the DNA molecules comprising the portion of the region of interest. In some embodiments, analyzing comprises sequencing the enriched DNA molecules to produce a plurality of cell-free DNA sequencing reads. In some embodiments, analyzing comprises first enriching the DNA molecules comprising the portion of the region of interest, and second sequencing the DNA molecules comprising the portion of the region of interest. In some embodiments, analyzing comprises subjecting the enriched DNA molecules to digital PCR produce a plurality of cell-free DNA sequencing reads.

In some embodiments, there is provided a method of detecting the presence or absence of a genetic variant in a region of interest in the genome of a fetus in a pregnant woman. In some embodiments, the method comprises obtaining cell-free DNA from a plasma sample of the pregnant woman; preparing a DNA library from said cell-free DNA, wherein the DNA library comprises a plurality of DNA molecules (which can comprise a molecular barcode); obtaining an enriched population of DNA molecules from said DNA library, wherein the enriched population of DNA molecules comprise the region of interest; sequencing the enriched DNA molecules to produce a plurality of cell-free DNA sequencing reads; and detecting the presence or absence of the fetal genetic variant based on the cell-free DNA sequencing reads. In some embodiments, the method comprises obtaining an enriched population of DNA molecules from a DNA library comprising a plurality of DNA molecules (wherein the DNA molecules in the plurality of DNA molecules can comprise a molecular barcode), wherein the DNA library is prepared from cell-free DNA in a plasma sample of the pregnant woman, and wherein the enriched population of DNA molecules comprise the region of interest; sequencing the enriched DNA molecules to produce a plurality of cell-free DNA sequencing reads; and detecting the presence or absence of the fetal genetic variant based on the cell-free DNA sequencing reads. In some embodiments, the method comprises obtaining cell-free DNA from a plasma sample of the pregnant woman; preparing a DNA library from said cell-free DNA, wherein the DNA library comprises a plurality of DNA molecules (wherein the DNA molecules in the plurality of DNA molecules can comprise a molecular barcode); sequencing a portion of the DNA library to produce a plurality of cell-free DNA sequencing reads, wherein the portion of the DNA library is enriched for DNA molecules comprising the region of interest; and detecting the presence or absence of the fetal genetic variant based on the cell-free DNA sequencing reads.

In some embodiments, there is provided a method of detecting the presence or absence of a genetic variant in a region of interest in the genome of a fetus in a pregnant woman comprising (a) preparing a DNA library form cell-free DNA, wherein the DNA library comprises a plurality of DNA molecules comprising molecular barcodes; (b) enriching a population of DNA molecules from said DNA library, wherein the enriched population of DNA molecules comprise the region of interest or a portion thereof; (c) sequencing the enriched population of DNA molecules to produce a plurality of cell-free DNA sequencing reads; (d) sequencing a corresponding region of interest from the genome of the pregnant woman to produce a plurality of maternal sequencing reads; (e) computing a maternal allele frequency for the maternal sequencing reads; (f) computing a cell-free DNA allele frequency for the cell-free DNA sequencing reads; and (g) detecting the presence or absence of the fetal genetic variant by comparing the maternal allele frequency to the cell-free DNA allele frequency.

In some embodiments, there is provided a method of detecting the presence or absence of a genetic variant in a region of interest in the genome of a fetus in a pregnant woman comprising (a) preparing a DNA library form cell-free DNA, wherein the DNA library comprises a plurality of DNA molecules comprising molecular barcodes; (b) enriching a population of DNA molecules from said DNA library, wherein the enriched population of DNA molecules comprise the region of interest or a portion thereof; (c) sequencing the enriched population of DNA molecules to produce a plurality of cell-free DNA sequencing reads; (d) sequencing a corresponding region of interest from the genome of the pregnant woman to produce a plurality of maternal sequencing reads; (e) constructing a maternal haplotype; (f) computing a maternal allele frequency for the maternal haplotype; (g) computing a cell-free DNA allele frequency for the cell-free DNA sequencing reads; and (h) detecting the presence or absence of the fetal genetic variant by comparing the maternal allele frequency to the cell-free DNA allele frequency.

In some embodiments, there is provided a method of detecting the presence or absence of a small nucleotide polymorphism genetic variant in a region of interest in the genome of a fetus in a pregnant woman comprising (a) preparing a DNA library form cell-free DNA, wherein the DNA library comprises a plurality of DNA molecules comprising molecular barcodes; (b) enriching a population of DNA molecules from said DNA library, wherein the enriched population of DNA molecules comprise the region of interest or a portion thereof; (c) sequencing the enriched population of DNA molecules to produce a plurality of cell-free DNA sequencing reads; (d) sequencing a corresponding region of interest from the genome of the pregnant woman to produce a plurality of maternal sequencing reads; (e) computing a maternal allele frequency for the maternal sequencing reads; (f) computing a cell-free DNA allele frequency for the cell-free DNA sequencing reads; and (g) detecting the presence or absence of the small nucleotide polymorphism fetal genetic variant by comparing the maternal allele frequency to the cell-free DNA allele frequency, wherein the molecular barcode is used to distinguish the small nucleotide polymorphism fetal genetic variant from a random or systematic error.

In some embodiments, there is provided a method of detecting the presence or absence of a small nucleotide polymorphism genetic variant in a region of interest in the genome of a fetus in a pregnant woman comprising (a) preparing a DNA library form cell-free DNA, wherein the DNA library comprises a plurality of DNA molecules comprising molecular barcodes; (b) enriching a population of DNA molecules from said DNA library, wherein the enriched population of DNA molecules comprise the region of interest or a portion thereof; (c) sequencing the enriched population of DNA molecules to produce a plurality of cell-free DNA sequencing reads; (d) sequencing a corresponding region of interest from the genome of the pregnant woman to produce a plurality of maternal sequencing reads; (e) constructing a maternal haplotype; (f) computing a maternal allele frequency for the maternal haplotype; (g) computing a cell-free DNA allele frequency for the cell-free DNA sequencing reads; and (h) detecting the presence or absence of the fetal genetic variant by comparing the maternal allele frequency to the cell-free DNA allele frequency, wherein the molecular barcode is used to distinguish the small nucleotide polymorphism fetal genetic variant from a random or systematic error.

In some embodiments, there is provided a method of detecting the presence or absence of a copy number variant in a region of interest in the genome of a fetus in a pregnant woman comprising (a) preparing a DNA library form cell-free DNA, wherein the DNA library comprises a plurality of DNA molecules comprising molecular barcodes; (b) enriching a population of DNA molecules from said DNA library, wherein the enriched population of DNA molecules comprise the region of interest or a portion thereof; (c) sequencing the enriched population of DNA molecules to produce a plurality of cell-free DNA sequencing reads; (d) sequencing a corresponding region of interest from the genome of the pregnant woman to produce a plurality of maternal sequencing reads; (e) computing a maternal allele frequency for the maternal sequencing reads; (f) computing a cell-free DNA allele frequency for the cell-free DNA sequencing reads; and (g) detecting the presence or absence of the copy number variant by comparing the maternal allele frequency to the cell-free DNA allele frequency, wherein the molecular barcode is used to filter out redundantly counted DNA sequences.

In some embodiments, there is provided a method of detecting the presence or absence of a copy number variant in a region of interest in the genome of a fetus in a pregnant woman comprising (a) preparing a DNA library form cell-free DNA, wherein the DNA library comprises a plurality of DNA molecules comprising molecular barcodes; (b) enriching a population of DNA molecules from said DNA library, wherein the enriched population of DNA molecules comprise the region of interest or a portion thereof; (c) sequencing the enriched population of DNA molecules to produce a plurality of cell-free DNA sequencing reads; (d) sequencing a corresponding region of interest from the genome of the pregnant woman to produce a plurality of maternal sequencing reads; (e) constructing a maternal haplotype; (f) computing a maternal allele frequency for the maternal haplotype; (g) computing a cell-free DNA allele frequency for the cell-free DNA sequencing reads; and (h) detecting the presence or absence of the copy number variant by comparing the maternal allele frequency to the cell-free DNA allele frequency, wherein the molecular barcode is used to filter out redundantly counted DNA sequences.

In some embodiments, there is provided a method of detecting the presence or absence of a microdeletion in a region of interest in the genome of a fetus in a pregnant woman comprising (a) preparing a DNA library form cell-free DNA, wherein the DNA library comprises a plurality of DNA molecules comprising molecular barcodes; (b) enriching a population of DNA molecules from said DNA library, wherein the enriched population of DNA molecules comprise the region of interest or a portion thereof; (c) sequencing the enriched population of DNA molecules to produce a plurality of cell-free DNA sequencing reads; (d) sequencing a corresponding region of interest from the genome of the pregnant woman to produce a plurality of maternal sequencing reads; (e) computing a maternal allele frequency for the maternal sequencing reads; (f) computing a cell-free DNA allele frequency for the cell-free DNA sequencing reads; and (g) detecting the presence or absence of the microdeletion by comparing the maternal allele frequency to the cell-free DNA allele frequency, wherein the molecular barcode is used to filter out redundantly counted DNA sequences.

In some embodiments, there is provided a method of detecting the presence or absence of a microdeletion in a region of interest in the genome of a fetus in a pregnant woman comprising (a) preparing a DNA library form cell-free DNA, wherein the DNA library comprises a plurality of DNA molecules comprising molecular barcodes; (b) enriching a population of DNA molecules from said DNA library, wherein the enriched population of DNA molecules comprise the region of interest or a portion thereof; (c) sequencing the enriched population of DNA molecules to produce a plurality of cell-free DNA sequencing reads; (d) sequencing a corresponding region of interest from the genome of the pregnant woman to produce a plurality of maternal sequencing reads; (e) constructing a maternal haplotype; (f) computing a maternal allele frequency for the maternal haplotype; (g) computing a cell-free DNA allele frequency for the cell-free DNA sequencing reads; and (h) detecting the presence or absence of the microdeletion by comparing the maternal allele frequency to the cell-free DNA allele frequency, wherein the molecular barcode is used to filter out redundantly counted DNA sequences.

In some embodiments, the cell-free DNA is obtained from the plasma of the pregnant woman. In some embodiments, whole blood is withdrawn from the pregnant woman and separated, for example by centrifugation (e.g., density gradient centrifugation). Preferably, lysis of blood cells, such as maternal leukocytes is minimized to avoid diluting the proportion of cell-free DNA from the fetal genome in the sample. Streck tubes, for example, are known to minimize lysis of leukocytes, and provide an adequate collection vessel for the whole blood. In some embodiments, the buffy coat of the centrifuged sample is retained separately from the plasma. The buffy coat includes leukocytes separated from the red blood cells and the plasma, but includes none or essentially none of the cell-free DNA. Thus, in some embodiments, the maternal DNA can be extracted from the buffy coat and used for sequencing or constructing a maternal haplotype.

Generally, sufficient cell-free DNA from the fetal genome is present in the plasma of a pregnant woman (i.e., maternal plasma) starting at about 10 weeks gestational age to perform the methods described herein, although occasionally sufficient cell-free DNA from the fetal genome can be detected even earlier. In some embodiments, the gestational age of the fetus is about 6 weeks or older, about 8 weeks or older, about 10 weeks or older, about 12 weeks or older, about 14 weeks or older, about 16 weeks or older, about 20 weeks or older, or about 24 weeks or older.

One or more predetermined regions of interest of the genome can be selected for genetic variant detection. In some embodiments, 1 or more, 2 or more, 3 or more, 4 or more, 5 or more, 6 or more, 7 or more, 8 or more, 9 or more, 10 or more, 15 or more, or 20 or more regions of interest are selected. In some embodiments, the region of interest is a gene or a fragment of a gene. Exemplary regions of interest include the FGFR3 gene (which is linked to achondroplasia and thanatophoric dysplasia), the Duchenne muscular dystrophy (DMD) gene, the Becker muscular dystrophy (BMD) gene, and the CFTR gene (which is linked to cystic fibrosis). The region of interest can be of any length, but is generally on the order of a single gene or a fragment thereof. In some embodiments, the region of interest comprises about 10,000,000 base pairs or fewer, about 9,000,000 base pairs or fewer, about 8,000,000 base pairs or fewer, about 7,000,000 base pairs or fewer, about 6,000,000 base pairs or fewer, about 5,000,000 base pairs or fewer, about 4,500,000 base pairs or fewer, about 4,000,000 base pairs or fewer, about 3,500,000 base pairs or fewer, about 3,000,000 base pairs or fewer, about 2,500,000 base pairs or fewer, about 2,000,000 base pairs or fewer, about 1,500,000 base pairs or fewer, about 1,000,000 base pairs or fewer, about 900,000 base pairs or few, about 800,000 base pairs or fewer, about 700,000 base pairs or fewer, about 600,000 base pairs or fewer, about 500,000 base pairs or fewer, about 450,000 base pairs or fewer, about 400,000 base pairs or fewer, about 350,000 base pairs or fewer, about 300,000 base pairs or fewer, about 250,000 base pairs or fewer, about 200,000 base pairs or fewer, about 175,000 base pairs or fewer, about 150,000 base pairs or fewer, about 125,000 base pairs or fewer, about 100,000 base pairs or fewer, about 90,000 base pairs or fewer, about 80,000 base pairs or fewer, about 70,000 base pairs or fewer, about 60,000 base pairs or fewer, about 50,000 base pairs or fewer, about 40,000 base pairs or fewer, about 30,000 base pairs or fewer, about 25,000 base pairs or fewer, about 20,000 base pairs or fewer, about 10,000 base pairs or fewer, or about 5,000 base pairs or fewer. In some embodiments, the region of interest encodes mRNA, miRNA, snoRNA, rRNA, snRNA, ncRNA, a genetic regulatory region, an intron, or an exon.

In some embodiments, the method comprises preparing a DNA library (which comprises a plurality of DNA molecules) from the cell-free DNA. In some embodiments, the method further comprises preparing a DNA library (which comprises a plurality of DNA molecules) from maternal and/or paternal genomic DNA. In some embodiments, the DNA molecules are about 50 to about 1000 base pairs in length, such about 50 to about 100 base pairs in length, about 100 to about 150 base pairs in length, about 150 to about 200 base pairs in length, about 200 to about 250 base pairs in length, about 250 to about 300 base pairs in length, about 300 to about 400 base pairs in length, about 400 to about 500 base pairs in length, about 500 to about 600 base pairs in length, about 600 to about 700 base pairs in length, about 700 to about 800 base pairs in length, about 800 to about 900 base pairs in length, or about 900 to about 1000 base pairs in length. This library can be used for the methods described herein. The DNA library can be formed prior to or simultaneous to enriching the region of interest, depending on which enrichment method is performed. For example, in some embodiments, the DNA library is formed prior to enrichment using a hybrid-capture method. In some embodiments, the DNA library is formed during enrichment, such as when enrichment is performed using molecular inversion probes or PCR amplification of the region of interest or a portion thereof.

In some embodiment, oligonucleotides are incorporated into the DNA molecule (i.e., attached to the 5' terminus of the DNA molecule), for example when forming the DNA library. The oligonucleotides can be incorporated before or during enrichment of the DNA molecule. The oligonucleotides can comprise one or more of a molecular barcode, an adapter sequence, or a sample-specific sequence. In some embodiments, a molecular barcode is ligated to the DNA molecule. In some embodiments, the molecular barcode is used to minimize random or systematic errors that may arise. For example, the molecular barcode can be used to distinguish a single nucleotide polymorphism call or a copy number variant call from a random or systematic error.

The cell-free DNA can be enriched at one or more regions of interest using the techniques described herein. For example, in some embodiments the cell-free DNA is enriched using hybrid capture, molecular inversion probes, PCR amplification, or simultaneous sequencing and enrichment (such as preferentially sequencing molecules from a region of interest). For more on enriching genomic regions, see below and Mertes et al., Targeted enrichment of genomic DNA regions for next-generation sequencing, *Briefings in Functional Genomics*, vol. 10(6), pp. 374-386 (2011).

In some embodiments, a DNA library is prepared from the cell-free DNA, followed by enrichment of DNA molecules comprising a portion of the region of interest. Cell-free DNA typically has fragment sizes that are useful for downstream analysis (such as sequencing or digital PCR). In some embodiments, a molecular barcode is incorporated into the DNA molecules, for example by ligating the molecular barcode to the 5'-end of the DNA molecule. The DNA molecules comprising the region of interest or a portion of the region of interest are enriched, for example by using hybridization probes. This process allows DNA molecules that comprise the region of interest or a portion of the region of interest in the DNA library to be separated from DNA molecules that do not comprise the region of interest or a portion of the region of interest. In some embodiments the molecular barcode is part of an oligonucleotide that further comprises a sequencing primer. The enriched DNA molecules can then be subjected to further analysis, for example sequencing or digital PCR, to generate reads and allele frequencies.

In some embodiments, library preparation and enrichment occur simultaneously. For example in some embodiments, the cell-free DNA is combined with an oligonucleotide that comprises a molecular barcode and a sample-specific sequence, which targets a sequence within a region of interest. PCR can be used, for example, to enrich the region of interest or a portion thereof, as well as generate the DNA library (which can, depending on the oligonucleotide used, comprise molecular barcodes and/or sequencing adapters fused to the plurality of DNA molecules). The enriched DNA molecules can then be subjected to further analysis, for example sequencing or digital PCR, to generate reads and allele frequencies.

In some embodiments, the DNA library is prepared; followed by preferentially analyzing the DNA molecules. In some embodiments, the DNA library prepared by ligating a molecular barcode and/or an adapter sequence to the DNA molecules in the DNA library. In some embodiments, the analysis comprises simultaneous sequencing and enrichment of the regions of interest. Preferential analysis, such as preferential sequencing, selectively analyzes DNA molecules that comprise a region of interest or a portion thereof.

In some embodiments, the maternal genome or a portion of the maternal genome is analyzed, for example by sequencing or by digital PCR. For example, in some embodiments, a region of interest in the maternal genome which corresponds to the region of interest in the fetal genome is analyzed. A maternal DNA library can be constructed comprising DNA molecules from the maternal genome. In some embodiments, constructing the maternal DNA library comprises fragmenting the maternal genome. The maternal DNA molecules are optionally enriched for a region of interest that corresponds with the region of interest in the fetal genome, or a segment thereof. In some embodiments, the maternal DNA molecules are analyzed, for example by sequencing or digital PCR to generate maternal sequencing reads and/or to compute a maternal allele frequency for the maternal sequencing reads.

In some embodiments, a maternal haplotype is constructed. For example, the maternal haplotype can be constructed by phasing genetic variants present in the maternal sequencing reads, by sequencing a corresponding region of interest in a biological relative of the pregnant woman, or by statistical mapping methods.

In some embodiments, a maternal allele frequency is compared to a cell-free DNA allele frequency. This comparison allows for the detection of fetal genetic variants. In some embodiments the fetal genetic variant detected is a small nucleotide polymorphism, such as a single nucleotide variant, a multi-nucleotide variant, or an indel variant (such as an insertion variant or a deletion variant) of about 100 base pairs or smaller. Such small nucleotide polymorphism variants can be de novo variants or inherited variants (either maternally or paternally). In some embodiments, the small nucleotide polymorphism fetal genetic variants are detected by computing a cell-free DNA allele frequency; computing a maternal allele frequency; and comparing the cell-free DNA allele frequency and the maternal allele frequency. A relative increase or decrease in allele frequency of the cell-free DNA compared to the maternal genome indicates the presence of a variant, and a small nucleotide polymorphism variant can be called (that is, the small nucleotide polymorphism variant is present). In some embodiments, the relative increase or decrease in allele frequency is determined beyond a predetermined threshold before a [SNP] small nucleotide polymorphism variant is called (that is, the small nucleotide polymorphism variant is present). If there is no relative increase or decrease (or no relative increase or decrease beyond a predetermined threshold), then no small nucleotide polymorphism variant is called (that is, the small nucleotide polymorphism variant is absent). In some embodiments, a maternal haplotype is employed for higher resolution.

In some embodiments, the fetal genetic variant is a copy number variant, such as a copy number loss variant. In some embodiments, the copy number variant is about the length of an exome. In some embodiments, the copy number variant is between about 100 base pairs or more, about 200 base pairs or more, about 300 base pairs or more, about 400 base pairs or more, about 500 base pairs or more, about 1000 base pairs or more, about 2000 base pairs or more, about 3000 base pairs or more, about 4000 base pairs or more, about 5000 base pairs or more, or about 10,000 base pairs or more. The copy number variants can be detected by counting the number of copies of a given allele (e.g., a region of interest or a portion of a region of interest) in the cell-free DNA and comparing it to the number of copies of the allele in the maternal genome. A relative increase or decrease in allele frequency of the cell-free DNA compared to the maternal genome indicates the presence of a copy number variant, and a variant can be called (that is, the copy number variant is present). In some embodiments, the relative increase or decrease in allele frequency is determined beyond a predetermined threshold before a copy number variant is called (that is, the copy number variant is present). If there is no relative increase or decrease (or no relative increase or decrease beyond a predetermined threshold), then no copy number variant is called (that is, the small nucleotide polymorphism variant is absent).

In some embodiments, the paternal genome or a portion of the paternal genome is analyzed, for example by sequencing or by digital PCR. For example, in some embodiments, a region of interest in the paternal genome which corresponds to the region of interest in the fetal genome is analyzed. A paternal DNA library can be constructed comprising DNA molecules from the paternal genome. In some embodiments, constructing the paternal DNA library comprises fragmenting the paternal genome. The paternal DNA molecules are optionally enriched for a region of interest that corresponds with the region of interest in the fetal genome, or a segment thereof. In some embodiments, the paternal DNA molecules are analyzed, for example by sequencing or digital PCR to generate paternal sequencing reads and/or to compute a paternal allele frequency for the paternal sequencing reads. In some embodiments, a paternal haplotype is constructed. For example, the paternal haplotype can be constructed by phasing genetic variants present in the paternal sequencing reads, by sequencing a corresponding region of interest in a biological relative of the father, or by statistical mapping methods.

Further provided herein is a system for detecting the presence or absence of a genetic variant in a region of interest in the genome of a fetus in a pregnant woman, comprising a sequencing system that generates sequencing reads, wherein the sequencing read is generated by sequencing an enriched population of DNA molecules from a DNA library comprising a plurality of DNA molecules comprising molecular barcodes, wherein the DNA library is prepared from cell-free DNA in the blood sample of the pregnant woman, and wherein the enriched population of DNA molecules comprise the region of interest; and a data processing system for analyzing the sequencing reads to detect the presence or absence of the fetal genetic variant. In some embodiments, there is provided a computer-readable medium comprising codes that, upon execution of one or more processors, implements any one of the methods described herein.

FIG. 1 is a schematic of one embodiment of a method for detecting, and optionally verifying, the presence or absence of a paternally-inherited dominant or de novo fetal genetic variant. Briefly, targeted-enriched cell-free DNA from a pregnant woman is sequenced 10 and analyzed for the presence or absence of a paternally-inherited dominant or de novo fetal genetic variant 15. If no paternally-inherited dominant or de novo fetal genetic variant is detected 20, it is determined that there is an absence of a paternally-inherited dominant or de novo fetal genetic variant in a region of interest in the genome of the fetus 25. If a paternally-inherited dominant or de novo fetal genetic variant is detected, it is determined that there is a presence of a paternally-inherited dominant or de novo fetal genetic variant in a region of interest in the genome of the fetus.

Optionally, the presence or absence of the fetal genetic variant is verified. If a paternally-inherited dominant or de novo fetal genetic variant is detected 30, the presence of the paternally-inherited dominant or de novo fetal genetic variant in a region of interest can be confirmed by direct targeted sequencing of the fetal genome (for example, from a fetal sample such as acquired from amniocentesis, chorionic villus sampling, or percutaneous umbilical cord blood sampling) 35 and analyzing for a paternally-inherited dominant or de novo fetal genetic variant 40. Verification can further or alternatively include sequencing (and also optionally phasing) a maternal and/or paternal genome. If the presence of the paternally-inherited dominant or de novo fetal genetic variant in a region of interest is not confirmed 45, it is determined that there is an absence of a paternally-inherited dominant or de novo fetal genetic variant in a region of interest in the genome of the fetus 25. If the presence of the paternally-inherited dominant or de novo fetal genetic variant in a region of interest is confirmed 50, it is determined that there is a presence of a paternally-inherited dominant or de novo fetal genetic variant in a region of interest in the genome of the fetus 55.

Figure 2:
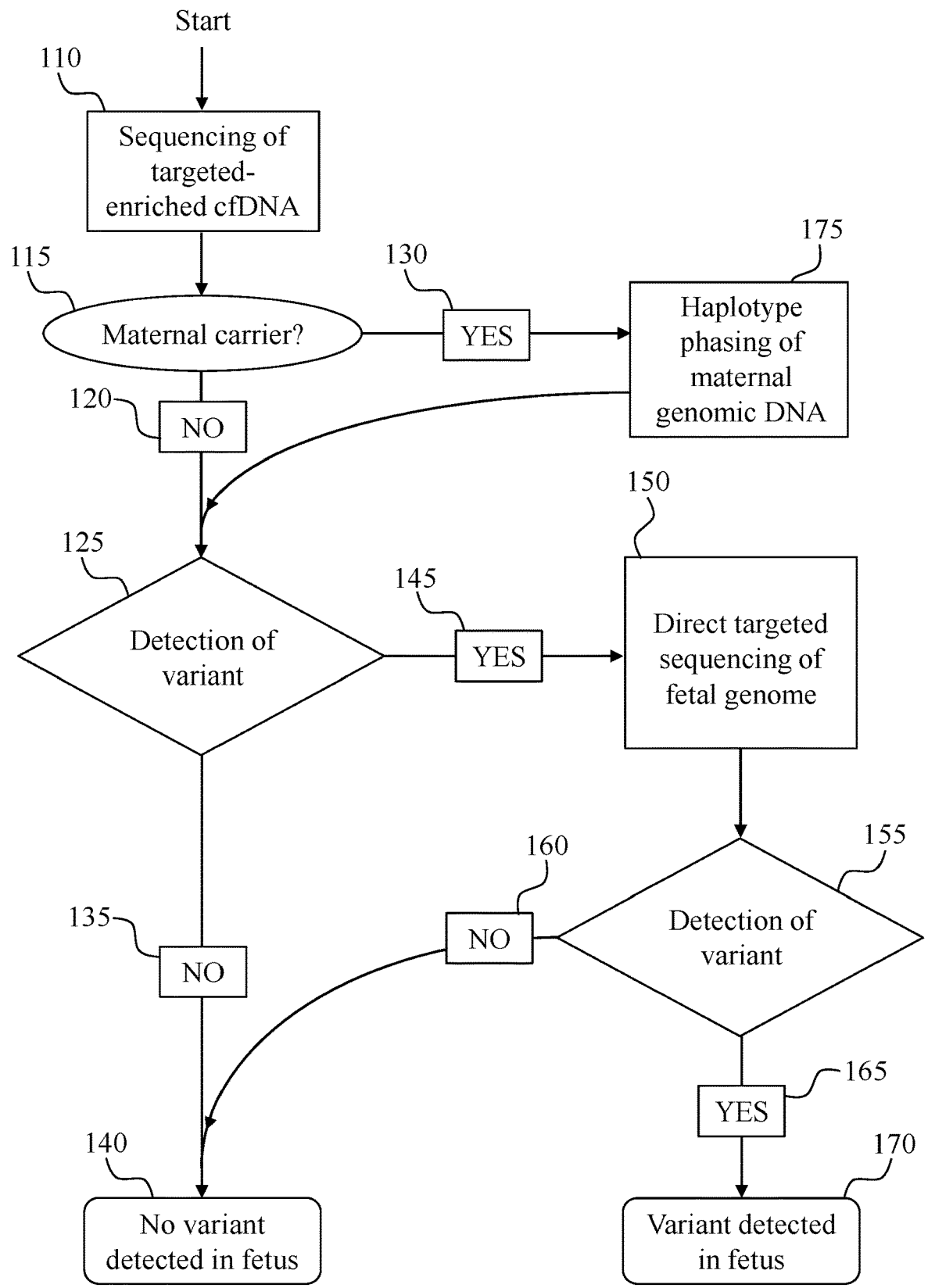
FIG. 2 is a schematic of one embodiment of a method for detecting, and optionally verifying, the presence or absence of a paternally-inherited dominant, maternally inherited-dominant, or de novo fetal genetic variant using haplotype phasing of maternal genomic DNA.

FIG. 2 is a schematic of one embodiment of a method for detecting, and optionally verifying, the presence or absence of a paternally-inherited dominant, maternally inherited-dominant, or de novo fetal genetic variant using haplotype phasing of maternal genomic DNA. Briefly, targeted-enriched cell-free DNA from a pregnant woman is sequenced 110. The carrier status of the mother for the genetic variant is optionally determined or known 115. If the mother is not a carrier for the genetic variant 120, the fetal sequences are analyzed for the presence or absence of a paternally-inherited dominant, maternally inherited-dominant, or de novo fetal genetic variant 125. If no a paternally-inherited dominant, maternally inherited-dominant, or de novo fetal genetic variant is detected 135, it is determined that there is an absence of a paternally-inherited dominant, maternally inherited-dominant, or de novo fetal genetic variant in a region of interest in the genome of the fetus 140. If the mother is a carrier 130, the maternal genomic DNA is sequenced and haplotype phased 175 and then the fetal sequences are analyzed for the presence or absence of a paternally-inherited dominant, maternally inherited-dominant, or de novo fetal genetic variant 125. Using the information from haplotype phasing of maternal genomic DNA, if no paternally-inherited dominant, maternally inherited-dominant, or de novo fetal genetic variant is detected 135, it is determined that there is an absence of a paternally-inherited dominant, maternally inherited-dominant, or de novo fetal genetic variant in a region of interest in the genome of the fetus 140. If a paternally-inherited dominant, maternally inherited-dominant, or de novo fetal genetic variant is detected, it is determined that there is a presence of a paternally-inherited dominant, maternally inherited-dominant, or de novo fetal genetic variant in a region of interest in the genome of the fetus.

Optionally, the presence or absence of the fetal genetic variant is verified. If a paternally-inherited dominant, maternally inherited-dominant, or de novo fetal genetic variant is detected 145, the presence of the paternally-inherited dominant, maternally inherited-dominant, or de novo fetal genetic variant in a region of interest can be confirmed by direct targeted sequencing of the fetal genome (for example, from a fetal sample such as acquired from amniocentesis, chorionic villus sampling, or percutaneous umbilical cord blood sampling) 150 and analyzing for a paternally-inherited dominant, maternally inherited-dominant, or de novo fetal genetic variant 155. Verification can further or alternatively include sequencing (and optionally haplotype phasing) a paternal genome. If the presence of the paternally-inherited dominant, maternally inherited-dominant, or de novo fetal genetic variant in a region of interest is not confirmed 160, it is determined that there is an absence of a paternally-inherited dominant, maternally inherited-dominant, or de novo fetal genetic variant in a region of interest in the genome of the fetus 140. If the presence of the paternally-inherited dominant, maternally inherited-dominant, or de novo fetal genetic variant in a region of interest is confirmed 165, it is determined that there is a presence of a paternally-inherited dominant, maternally inherited-dominant, or de novo fetal genetic variant in a region of interest in the genome of the fetus 170.

Figure 3:
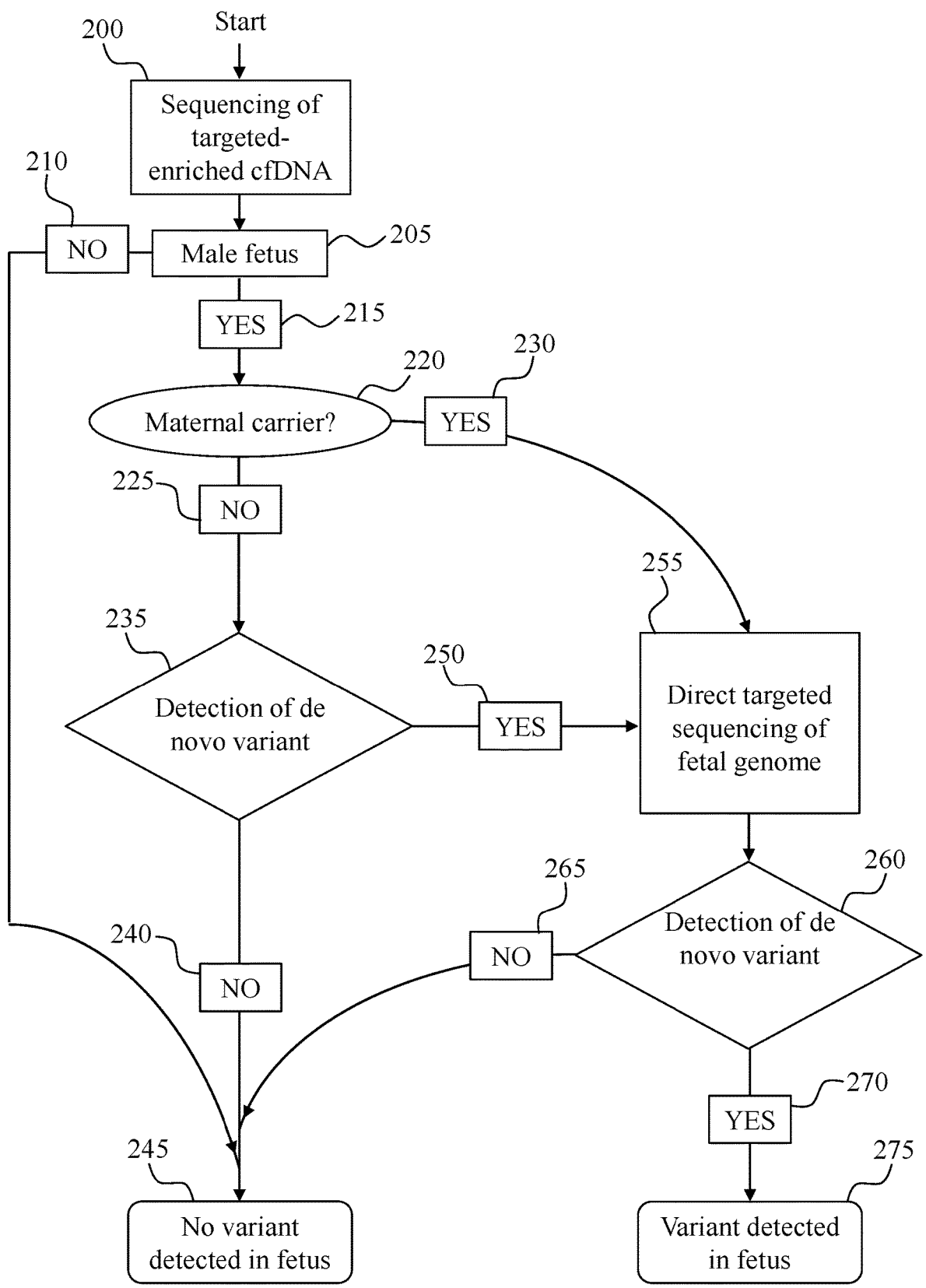
FIG. 3 is a schematic of one embodiment of a method for detecting, and optionally verifying, the presence or absence of an X-linked recessive fetal genetic variant, wherein the father is not phenotypically affected by the variant allele.

FIG. 3 is a schematic of one embodiment of a method for detecting, and optionally verifying, the presence or absence of an X-linked recessive fetal genetic variant, wherein the father is not phenotypically affected by the variant allele. Briefly, targeted-enriched cell-free DNA from a pregnant woman is sequenced 200. The sex of the fetus is optionally determined or known. If the fetus is not 210 a male 205, it is determined that there is an absence of an X-linked recessive fetal genetic variant in a region of interest in the genome of the fetus 245. If the fetus is a male 215, the carrier status of the mother for the genetic variant is optionally determined or known 220. If the mother is not a carrier for the genetic variant 225, the fetal sequences are analyzed for the presence or absence of an X-linked recessive fetal genetic variant 235. If no X-linked recessive fetal genetic variant is detected 240, it is determined that there is an absence of an X-linked recessive fetal genetic variant in a region of interest in the genome of the fetus 245. If an X-linked recessive fetal genetic variant is detected, it is determined that there is a presence of an X-linked recessive fetal genetic variant in a region of interest in the genome of the fetus.

Optionally, the presence or absence of the fetal genetic variant is verified. If the mother is a carrier of an X-linked recessive genetic variant 230 or if an X-linked recessive fetal genetic variant is detected from fetal sequences 250, the presence of the X-linked recessive fetal genetic variant in a region of interest can be confirmed by direct targeted sequencing of the fetal genome (for example, from a fetal sample such as acquired from amniocentesis, chorionic villus sampling, or percutaneous umbilical cord blood sampling) 255 and analyzing for an X-linked recessive fetal genetic variant 260. Verification can further or alternatively include sequencing (and optionally haplotype phasing) a maternal and/or paternal genome. If the presence of the X-linked recessive fetal genetic variant in a region of interest is not confirmed 265, it is determined that there is an absence of an X-linked recessive fetal genetic variant in a region of interest in the genome of the fetus 245. If the presence of the X-linked recessive fetal genetic variant in a region of interest is confirmed 270, it is determined that there is a presence of an X-linked recessive fetal genetic variant in a region of interest in the genome of the fetus 275.

Figure 4:
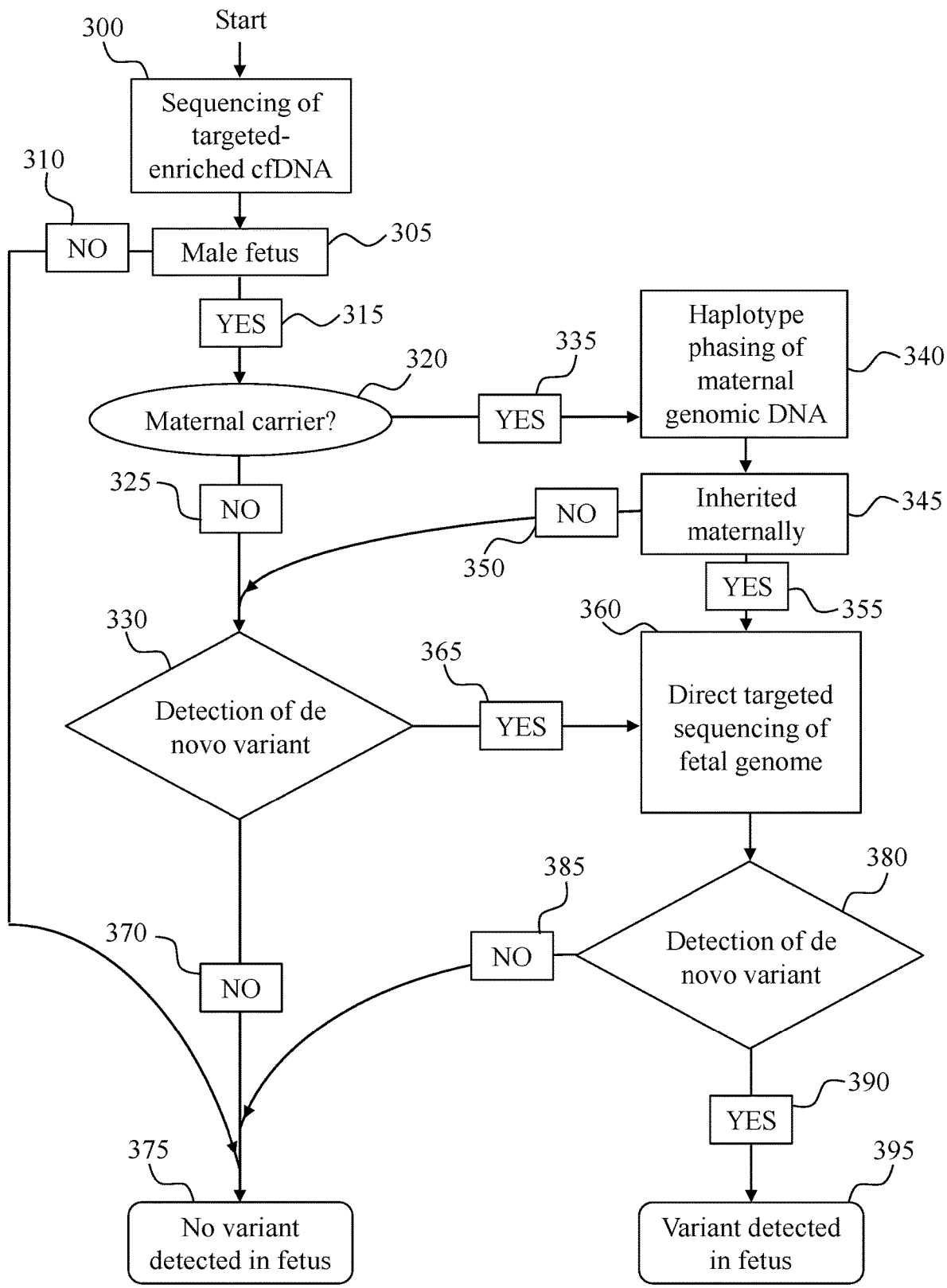
FIG. 4 is a schematic of one embodiment of a method for detecting, and optionally verifying, the presence or absence of an X-linked recessive fetal genetic variant, wherein the father is not phenotypically affected by the variant allele, using haplotype phasing of maternal genomic DNA.

FIG. 4 is a schematic of one embodiment of a method for detecting, and optionally verifying, the presence or absence of an X-linked recessive fetal genetic variant, wherein the father is not phenotypically affected by the variant allele, using haplotype phasing of maternal genomic DNA. Briefly, targeted-enriched cell-free DNA from a pregnant woman is sequenced 300. The sex of the fetus is optionally determined or known. If the fetus is not 310 a male 305, it is determined that there is an absence of an X-linked recessive fetal genetic variant in a region of interest in the genome of the fetus 375. If the fetus is a male 315, the carrier status of the mother for the genetic variant is optionally determined or known 320. If the mother is not a carrier for the genetic variant 325, the fetal sequences are analyzed for the presence or absence of an X-linked recessive fetal genetic variant 330. If no X-linked recessive fetal genetic variant is detected 370, it is determined that there is an absence of an X-linked recessive fetal genetic variant in a region of interest in the genome of the fetus 375. If an X-linked recessive fetal genetic variant is detected, it is determined that there is a presence of an X-linked recessive fetal genetic variant in a region of interest in the genome of the fetus. If the mother is a carrier 335, the maternal genomic DNA is sequenced and haplotype phased 340 and then the fetal sequences are analyzed to determine if the variant is inherited from the mother 345. If the variant is not inherited from the mother 350, and using the information from haplotype phasing of maternal genomic DNA, if no X-linked recessive fetal genetic variant is detected 370, it is determined that there is an absence of an X-linked recessive fetal genetic variant in a region of interest in the genome of the fetus 375. Using the information from haplotype phasing of maternal genomic DNA, if an X-linked recessive fetal genetic variant is detected, it is determined that there is a presence of an X-linked recessive fetal genetic variant in a region of interest in the genome of the fetus.

Optionally, the presence or absence of the fetal genetic variant is verified. If the mother is a carrier of an X-linked recessive genetic variant and the variant is inherited from the mother 355 or if an X-linked recessive fetal genetic variant is detected from fetal sequences 365, the presence of the X-linked recessive fetal genetic variant in a region of interest can be confirmed by direct targeted sequencing of the fetal genome (for example, from a fetal sample such as acquired from amniocentesis, chorionic villus sampling, or percutaneous umbilical cord blood sampling) 360 and analyzed for an X-linked recessive fetal genetic variant 380. Verification can further or alternatively include sequencing (and optionally haplotype phasing) a paternal genome. If the presence of the X-linked recessive fetal genetic variant in a region of interest is not confirmed 385, it is determined that there is an absence of an X-linked recessive fetal genetic variant in a region of interest in the genome of the fetus 375. If the presence of the X-linked recessive fetal genetic variant in a region of interest is confirmed 390, it is determined that there is a presence of an X-linked recessive fetal genetic variant in a region of interest in the genome of the fetus 395.

Figure 5:
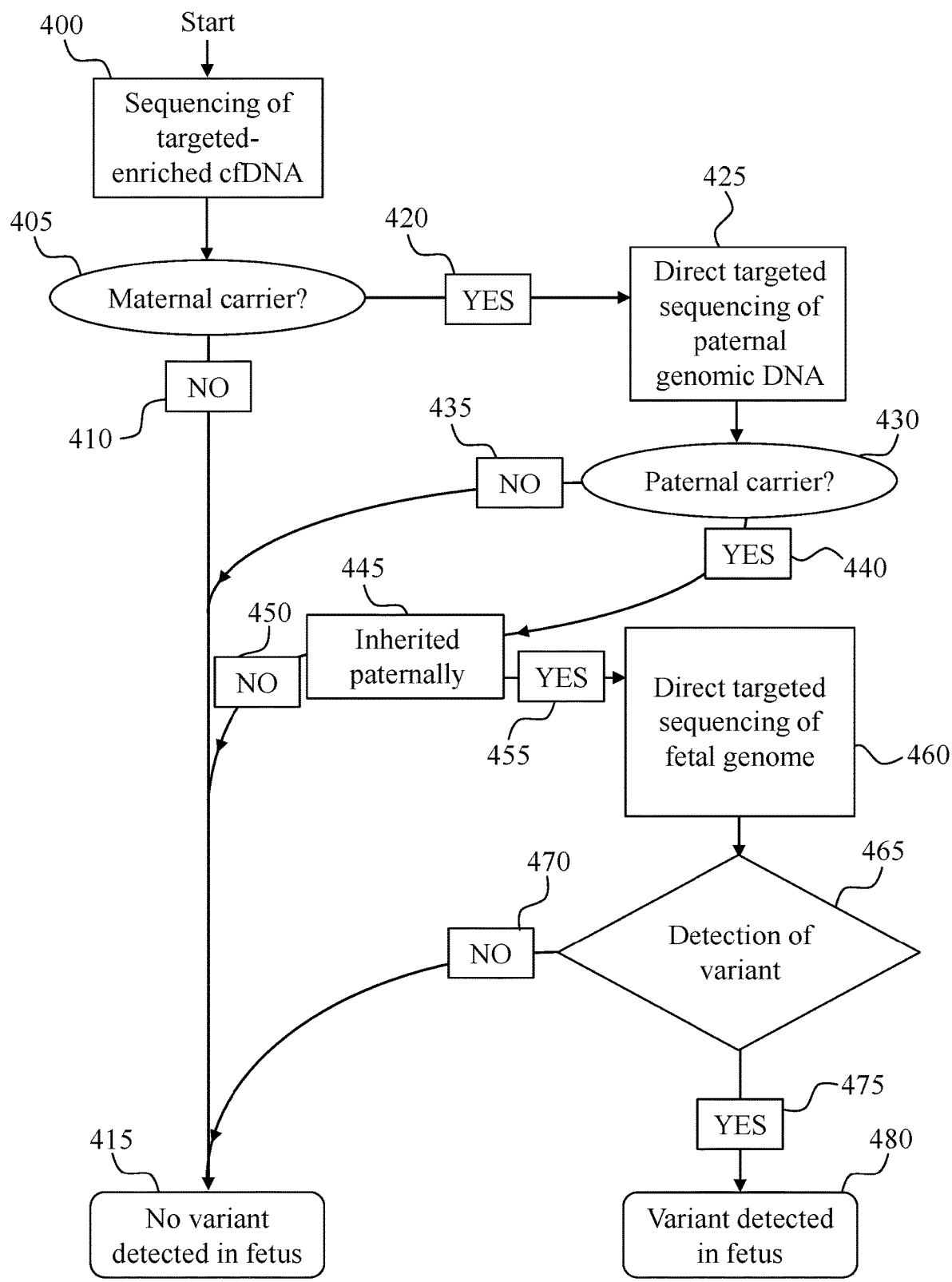
FIG. 5 is a schematic of one embodiment of a method for detecting, and optionally verifying, the presence or absence of an autosomal recessive fetal genetic variant.

FIG. 5 is a schematic of one embodiment of a method for detecting, and optionally verifying, the presence or absence of an autosomal recessive fetal genetic variant. Briefly, targeted-enriched cell-free DNA from a pregnant woman is sequenced 400. The carrier status of the mother for the genetic variant is optionally determined or known 405. If the mother is not a carrier for the genetic variant 410, it is determined that there is an absence of an autosomal recessive fetal genetic variant in a region of interest in the genome of the fetus 415. If the mother is a carrier for the genetic variant 420 or the carrier status of the mother is not determined, the paternal genomic DNA is optionally sequenced 425 and analyzed to assess if the father is a carrier of the genetic variant 430. If the father is not a carrier 435, it is determined that there is an absence of an autosomal recessive fetal genetic variant in a region of interest in the genome of the fetus 415. If the father is a carrier of the genetic variant 440 or the carrier status of the father is not determined, the fetal sequence is assessed to determine if a genetic variant was inherited from the father 445. If a genetic variant was not inherited from the father 450, it is determined that there is an absence of an autosomal recessive fetal genetic variant in a region of interest in the genome of the fetus 415. If a genetic variant inherited from the father is detected, it is determined that there is a presence of an autosomal recessive fetal genetic variant in a region of interest in the genome of the fetus.

Optionally, the presence or absence of the fetal genetic variant is verified. If a genetic variant inherited from the father is detected 455, the presence of the autosomal recessive fetal genetic variant in a region of interest can be confirmed by direct targeted sequencing of the fetal genome (for example, from a fetal sample such as acquired from amniocentesis, chorionic villus sampling, or percutaneous umbilical cord blood sampling) 460 and analyzed for an autosomal recessive fetal genetic variant 465. Verification can further or alternatively include sequencing a maternal genome. If the presence of the autosomal recessive fetal genetic variant in a region of interest is not confirmed 470, it is determined that there is an absence of an autosomal recessive fetal genetic variant in a region of interest in the genome of the fetus 415. If the presence of the autosomal recessive fetal genetic variant in a region of interest is confirmed 475, it is determined that there is a presence of an autosomal recessive fetal genetic variant in a region of interest in the genome of the fetus 480.

Figure 6:
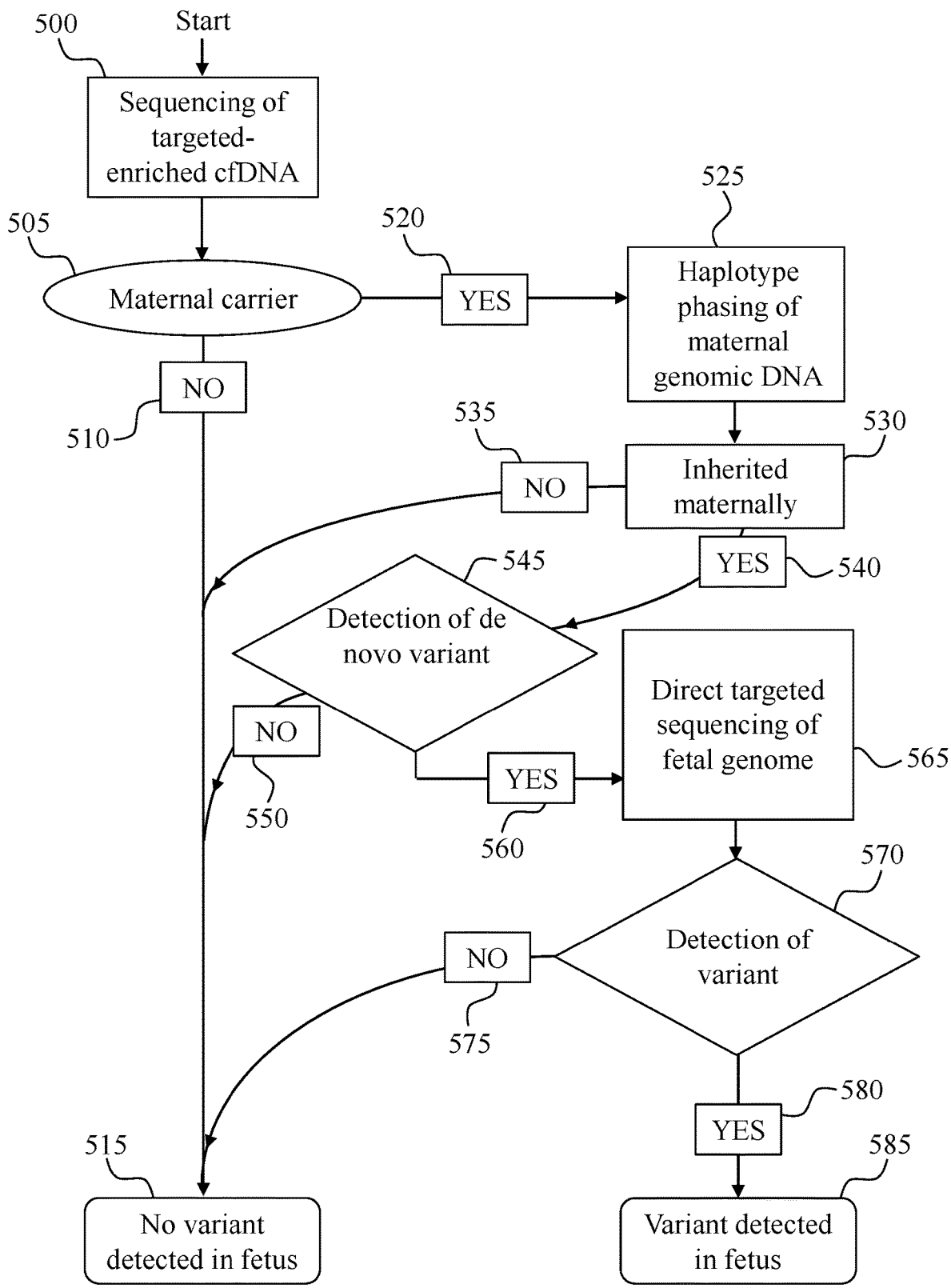
FIG. 6 is a schematic of one embodiment of a method for detecting, and optionally verifying, the presence or absence of an autosomal recessive fetal genetic variant using haplotype phasing of maternal genomic DNA.

FIG. 6 is a schematic of one embodiment of a method for detecting, and optionally verifying, the presence or absence of an autosomal recessive fetal genetic variant using haplotype phasing of maternal genomic DNA. Briefly, targeted-enriched cell-free DNA from a pregnant woman is sequenced 500. The carrier status of the mother for the genetic variant is optionally determined or known 505. If the mother is not a carrier for the genetic variant 510, it is determined that there is an absence of an autosomal recessive fetal genetic variant in a region of interest in the genome of the fetus 515. If the mother is a carrier for the genetic variant 520 or the carrier status of the mother is not determined, the maternal genomic DNA is sequenced and haplotype phased 525 and then the fetal sequences are analyzed to determine if the variant is inherited from the mother 530. If the variant is not inherited from the mother 535, it is determined that there is an absence of an autosomal recessive fetal genetic variant in a region of interest in the genome of the fetus 515. If the variant is inherited from the mother 540, the fetal sequences are analyzed for the presence or absence of an autosomal recessive fetal genetic variant 545. If no genetic variant is detected 550, it is determined that there is an absence of an autosomal recessive fetal genetic variant in a region of interest in the genome of the fetus 515. If a genetic variant is detected, it is determined that there is an absence of an autosomal recessive fetal genetic variant in a region of interest in the genome of the fetus.

Optionally, the presence or absence of the fetal genetic variant is verified. If a genetic variant is detected 560, the presence of the autosomal recessive fetal genetic variant in a region of interest can be confirmed by direct targeted sequencing of the fetal genome (for example, from a fetal sample such as acquired from amniocentesis, chorionic villus sampling, or percutaneous umbilical cord blood sampling) 565 and analyzed for an autosomal recessive fetal genetic variant 570. Verification can further or alternatively include sequencing a paternal genome. If the presence of the autosomal recessive fetal genetic variant in a region of interest is not confirmed 575, it is determined that there is an absence of an autosomal recessive fetal genetic variant in a region of interest in the genome of the fetus 515. If the presence of the autosomal recessive fetal genetic variant in a region of interest is confirmed 580, it is determined that there is a presence of an autosomal recessive fetal genetic variant in a region of interest in the genome of the fetus 585.

DNA Library Preparation

In some embodiments of the methods disclosed herein, a DNA library is obtained or prepared from cell-free DNA obtained from a pregnant woman. In some embodiments, a maternal DNA library is obtained or prepared from the maternal genome of the pregnant woman. In some embodiments, a paternal DNA library is obtained or prepared from a paternal genome. The DNA library comprises a population of DNA molecules. The DNA molecules are generally of sufficient length such that they can be accurately analyzed by sequencing or digital PCR. See, e.g., U.S. Pat. App. Nos. 2013/0225452 and 2012/0208705.

When producing a DNA library from genomic DNA, the genomic DNA can be fragmented, for example by using a hydrodynamic shear or other mechanical force, or fragmented by chemical or enzymatic digestion, such as restriction digesting. This fragmentation process allows the DNA molecules present in the genome to be sufficiently short for analysis, such as sequencing or digital PCR. Cell-free DNA, however, is generally sufficiently short such that no fragmentation is necessary. Cell-free DNA originates from genomic DNA. A portion of the cell-free DNA obtained from a plasma sample of a pregnant mother originates from the maternal genome and a portion of the cell-free DNA originates form the fetal genome.

In some embodiments, the DNA molecules are subjected to additional modification, resulting in the attachment of oligonucleotides to the DNA molecules. The oligonucleotides can comprise an adapter sequence or a molecular barcode (or both). In some embodiments, the adapter sequence is common to all oligonucleotides in a plurality of oligonucleotides that are used to form the DNA library. In some embodiments, the molecular barcodes are unique or have low redundancy. By way of example, the oligonucleotide can be attached to the DNA molecules by ligation. Direct attachment of the oligonucleotides to the DNA molecules in the DNA library can be used, for example, when enrichment occurs in a downstream process. For example, in some embodiments, a DNA library is prepared by direct attachment of an oligonucleotide comprising a molecular barcode and an adapter sequence, followed by enrichment (for example, by hybridization) of DNA molecules comprising a region of interest or a portion of a region of interest.

In some embodiments, library preparation and enrichment occurs simultaneously. For example, in some embodiments, DNA molecules comprising a region of interest or a portion thereof are preferentially amplified. This can be done, for example, by combining the cell-free DNA (or genomic DNA), with oligonucleotides comprising a target-specific sequence, an adapter sequence, and a molecular barcode, and amplifying the DNA molecules. As before, in some embodiments, the adapter sequence is common to all oligonucleotides in a plurality of oligonucleotides, and the molecular barcode is unique or of low redundancy. The target-specific sequence is unique to the targeted region of interest or portion thereof. Thus, PCR amplification selectively amplifies the DNA molecules comprising the region of interest or portion thereof.

When the methods include the use of tags or molecular barcodes, the tag or molecular barcode may also be ligated to the fragments or included within the ligated adapter sequences. The independent attachment of the tag or molecular barcode, as opposed to incorporating the tag or molecular barcode, may vary with the enrichment method. For example, when using hybrid capture-based target enrichment the adapter can include the molecular barcode, when using PCR-targeted enrichment target-specific primer pairs and overhangs are used that will incorporate the sequencing adapters and sample-specific and molecular barcodes, and when using on-sequencer enrichment the adapter may be separately ligated from the tag or molecular barcode.

Targeted Enrichment of a Region of Interest

The disclosure contemplates methods for enriching a target sequence in a region of interest. Enrichment techniques are known in the art. See, e.g., WO2013/112923; Mertes et al., *Targeted enrichment of genomic DNA regions for next-generation sequencing*, Briefings in Functional Genomics, vol. 10(6), pp. 374-386 (2011). Exemplary enrichment techniques include, but are not limited to, hybrid capture, selective circularization (also referred to as molecular inversion probes (MIP)), and PCR amplification of targeted regions of interest. Hybrid capture methods are based on the selective hybridization of the target genomic regions to user-designed oligonucleotides. The hybridization can be to oligonucleotides immobilized on high or low density microarrays (on-array capture), or solution-phase hybridization to oligonucleotides modified with a ligand (e.g., biotin) which can subsequently be immobilized to a solid surface, such as a bead (in-solution capture). Molecular inversion probe (MIP)-based method relies on construction of numerous single-stranded linear oligonucleotide probes, consisting of a common linker flanked by target-specific sequences. Upon annealing to a target sequence, the probe gap region is filled via polymerization and ligation, resulting in a circularized probe. The circularized probes are then released and amplified using primers directed at the common linker region. PCR-based methods employ highly parallel PCR amplification, where each target sequence in the sample has a corresponding pair of unique, sequence-specific primers. In some embodiments, enrichment of a target sequence occurs at the time of sequencing.

Sequencing

The disclosure contemplates methods of sequencing the sequence library. Sequencing may be by any method known in the art. Sequencing methods include, but are not limited to, Maxam-Gilbert sequencing-based techniques, chain-termination-based techniques, shotgun sequencing, bridge PCR sequencing, single-molecule real-time sequencing, ion semiconductor sequencing (Ion Torrent sequencing), nanopore sequencing, pyrosequencing (454), sequencing by synthesis, sequencing by ligation (SOLiD sequencing), sequencing by electron microscopy, dideoxy sequencing reactions (Sanger method), massively parallel sequencing, polony sequencing, and DNA nanoball sequencing. In some embodiments, sequencing involves hybridizing a primer to the template to form a template/primer duplex, contacting the duplex with a polymerase enzyme in the presence of a detectably labeled nucleotides under conditions that permit the polymerase to add nucleotides to the primer in a template-dependent manner, detecting a signal from the incorporated labeled nucleotide, and sequentially repeating the contacting and detecting steps at least once, wherein sequential detection of incorporated labeled nucleotide determines the sequence of the nucleic acid. In some embodiments, the sequencing comprises obtaining paired end reads. The accuracy or average accuracy of the sequence information may be greater than 80%, 90%, 95%, 99% or 99.98%. In some embodiments, the sequence information obtained is more than 50 bp, 100 bp or 200 bp. The sequence information may be obtained in less than 1 month, 2 weeks, 1 week 1 day, 3 hours, 1 hour, 30 minutes, 10 minutes, or 5 minutes. The sequence accuracy or average accuracy may be greater than 95% or 99%. The sequence coverage may be greater than 20 fold or less than 500 fold. Exemplary detectable labels include radiolabels, florescent labels, enzymatic labels, etc. In some embodiments, the detectable label may be an optically detectable label, such as a fluorescent label. Exemplary fluorescent labels include cyanine, rhodamine, fluorescien, coumarin, BODIPY, alexa, or conjugated multi-dyes. In some embodiments, the nucleotide is flagged if one or more of its sequence segments are substantially similar to one or more sequence segments of another nucleotide within the same partition.

It is also contemplated that some methods of sequencing the sequence library do not involve a prior target enrichment step. For example, use of on-sequencer enrichment, such as with a nanopore sequencer, allows for the "simultaneous" enrichment and sequencing of the sequence library by real-time rejection of molecules that are not from the region of interest. Alternatively, sequences can be selectively and preferentially sequenced from the region of interest.

Molecular Barcodes

In some embodiments, an identifier sequence, i.e., a molecular barcode is used to identify unique DNA molecules in a DNA library. See, e.g., U.S. Pat. App. Nos. 2013/0261019 and 2015/0080266. The molecular barcodes in some embodiments aid in reconstruction of a contiguous DNA sequences or assist in copy number variation determination. Exemplary markers include nucleic acid binding proteins, optical labels, nucleotide analogs, nucleic acid sequences, and others known in the art.

In some embodiments, the molecular barcode is a nanostructure barcode. In some embodiments, the molecular barcode comprises a nucleic acid sequence that when joined to a target polynucleotide serves as an identifier of the sample or sequence from which the target polynucleotide was derived. In some embodiments, molecular barcodes are at least 3, 4, 5, 6, 7, 8, 9, 10, 11, 12, 13, 14, 15, or more nucleotides in length. In some embodiments, molecular barcodes are shorter than 10, 9, 8, 7, 6, 5, or 4 nucleotides in length. In some embodiments, each molecular barcode in a plurality of molecular barcodes differ from every other molecular barcode in the plurality at least three nucleotide positions, such as at least 3, 4, 5, 6, 7, 8, 9, 10, or more positions. In some embodiments, molecular barcodes associated with some polynucleotides are of different length than molecular barcodes associated with other polynucleotides. In general, molecular barcodes are of sufficient length and comprise sequences that are sufficiently different to allow the identification of samples based on molecular barcodes with which they are associated. In some embodiments, both the forward and reverse adapter comprise at least one of a plurality of molecular barcode sequences. In some embodiments, each reverse adapter comprises at least one of a plurality of molecular barcode sequences, wherein each molecular barcode sequence of the plurality of molecular barcode sequences differs from every other molecular barcode sequence in the plurality of molecular barcode sequences.

Various sets of molecular barcodes have been reported in the literature. Several researchers have used sets that satisfy the conditions imposed by a Hamming Code (Hamady et al., *Error-correcting barcoded primers allow hundreds of samples to by pyrosequenced in multiplex*, Nature Methods, vol. 5(3), pp. 235-237 (2008); and Lefrançois et al., *Efficient yeast ChiP-Seq using multiplex short-read DNA sequencing*, BMC Genomics, vol. 10, pp. 1-18 (2009). Others have used sets that satisfy more complex conditions than a Hamming Code but share the similar guarantee of a certain minimal pairwise Hamming distance (Fierer et al., *The influence of sex, handedness, and washing on the diversity of hand surface bacteria*, Proc. Nat'l Adad. Sci., vol. 105, pp. 17,994-17,999 (2008); Krishnan et al., *Barcodes for DNA sequencing with guaranteed error correction and capability*, Electronics Letters, vol. 47, pp. 236-237 (2011). As an alternative to Hamming-distance based molecular barcodes, others have selected sets of molecular barcodes which satisfy a minimum pairwise edit distance. Sets of such molecular barcodes can work with insertion, deletion or substitution errors in the read of a barcode sequence.

In some embodiments, every molecular barcode in a set is unique, that is, any two molecular barcodes chosen out of a given set will differ in at least one nucleotide position. Furthermore, it is contemplated that molecular barcodes have certain biochemical properties that are selected based on how the set will be used. For example, certain sets of molecular barcodes that are used in an RT-PCR reaction should not have complementary sequences to any sequence in the genome of a certain organism or set of organisms. A requirement for non-complementarity helps to ensure that the use of a particular molecular barcode sequence will not result in mis-priming during molecular biological manipulations requiring primers, such as reverse transcription or PCR. Certain sets satisfy other biochemical properties imposed by the requirements associated with the processing of the sequence molecules into which the barcodes are incorporated.

Examples of sequencing technologies for sequencing molecular barcodes, as well as any generated nucleotide-based sequence, include, but are not limited to, Maxam-Gilbert sequencing-based techniques, chain-termination-based techniques, shotgun sequencing, bridge PCR sequencing, single-molecule real-time sequencing, ion semiconductor sequencing (Ion Torrent sequencing), nanopore sequencing, pyrosequencing (454), sequencing by synthesis, sequencing by ligation (SOLiD sequencing), sequencing by electron microscopy, dideoxy sequencing reactions (Sanger method), massively parallel sequencing, polony sequencing, and DNA nanoball sequencing.

In some embodiments, molecular barcodes are used to improve the power of copy-number calling algorithms by reducing non-independence from PCR duplication. In another embodiment, molecular barcodes can be used to improve test specificity by reducing sequence error generated during amplification.

Haplotype Phasing

In some embodiments, haplotypes of an individual, such as maternal haplotypes, paternal haplotypes, or fetal haplotypes are constructed. The haplotypes comprise alleles co-located on the same chromosome of the individual. The process is also known as "haplotype phasing" or "phasing". A haplotype may be any combination of one or more closely linked alleles inherited as a unit. The haplotypes may comprise different combinations of genetic variants. Artifacts as small as a single nucleotide polymorphism pair can delineate a distinct haplotype. Alternatively, the results from several loci could be referred to as a haplotype. For example, a haplotype can be a set of small nucleotide polymorphisms on a single chromatid that is statistically associated to be likely to be inherited as a unit.

Methods or assays used to determine haplotype involve determining a contiguous nucleic acid sequence of a given length. Contiguous sequences may be derived from an individual sequence read, including either short or long read-length sequencing. Long read-length sequencing technologies include, for example, single molecule sequencing, such as SMRT Sequencing and nanopore sequencing technologies. See, e.g., Koren et al., *One chromosome, one contig: Complete microbial genomes from long-read sequencing and assembly*, Curr. Opin. Microbiol., vol. 23, pp. 110-120 (2014); and Branton et al., *The potential and challenges of nanopore sequencing*, Nat. Biotechnol., vol. 26, pp. 1146-1153 (2008). Contiguous sequences may also be derived from assembly of sequence reads that are aligned and assembled based upon overlapping sequences within the reads. When using multiple sequence reads, haplotype phasing can be determined by physically partitioning the originating molecular structures or by using other known linkage data, e.g., the tagging with molecular barcodes as described elsewhere herein. These overlapping sequence reads may likewise include short reads, e.g., less than 500 bases, such as, in some cases from approximately 100 to 500 bases, and in some cases from 100 to 250 bases, or based upon longer sequence reads, e.g., greater than 500 bases, 1000 bases or even greater than 10,000 bases. The short reads are phased by using, for example, 10× or Illumina synthetic long read molecular phasing technology, trio (e.g., mother, father, and offspring) or other relatives' genomic information, or statistical haplotype information. In some embodiments, the haplotypes are constructed using statistical mapping. See, e.g., U.S. Pat. App. No. 2015/0376700, hereby incorporated by reference; and Browning et al., *Haplotype phasing: Exisiting methods and new developments*, Nat. Rev. Genet., vol. 12, pp. 703-714 (2012).

In some embodiments, the maternal haplotype is used to distinguish between a fetal genetic variant and a maternal genetic variant, or to determine which of the two maternal chromosomal loci was inherited by the fetus.

X-Linked Recessive Variant Detection

In some embodiments, provided herein is a method of detecting the presence or absence of a genetic variant in a region of interest in the genome of a fetus in a pregnant woman, wherein the fetal genetic variant is an X-linked recessive genetic variant. X-linked recessive disorders arise more frequently in male fetus because males with the disorder are hemizygous for the particular genetic variant. Example X-linked recessive disorders that can be detected using the methods described herein include Duchenne muscular dystrophy, Becker's muscular dystrophy, X-linked agammaglobulinemia, hemophilia A, and hemophilia B. These X-linked recessive variants can be inherited variants or de novo variants.

The methods described herein can be performed with or without constructing a maternal haplotype. Employing maternal haplotypes generally provides greater resolution of the fetal genetic variants, although substantial and accurate fetal genetic variant information can be resolved without constructing the maternal haplotype. In some embodiments, performing the method without maternal haplotypes allows for the accurate detection of large copy number variants (such as aneuploidy), microdeletions, paternally inherited X-linked recessive genetic variants, and de novo X-linked recessive genetic variants. In some embodiments, performing the method with maternal haplotypes allows for the accurate detection of large copy number variants (such as aneuploidy), microdeletions, paternally inherited X-linked recessive genetic variants, de novo X-linked recessive genetic variants, and maternally inherited X-linked genetic variants.

Cell-free DNA can be extracted from plasma of a pregnant woman (i.e., maternal plasma). The plasma comprises cell-free DNA from the fetal genome and cell-free DNA from the maternal genome. A DNA library is then formed from the cell-free DNA and the region of interest is enriched, thereby forming a population of enriched DNA molecules that correspond to the region of interest. The enriched DNA molecules are then sequenced to produce a plurality of cell-free sequencing reads. In some embodiments, molecular barcodes are employed. In some embodiments, the molecular barcodes are used to distinguish single nucleotide polymorphisms variants from random mutations. In some embodiments, the molecular barcodes are used to filter our redundantly counted DNA sequences.

The plurality of cell-free sequencing reads comprises sequencing reads from the fetal region of interest and sequencing reads from the maternal region of interest. An increase or decrease in the read frequency at a particular allele is computed, which indicates variance between the fetal genome and the maternal genome. A variant call can be made on the basis of that variance. In some embodiments, the variance is above (in the case of an increase in read frequency) or below (in the case of a decrease in read frequency) a predetermined threshold to trigger a variant call. Variance between the fetal and maternal genome for an X-linked region of interest is generally due to either a paternally inherited chromosome or a de novo mutation.

In addition to the accurate detection of large copy number variants (such as aneuploidy), microdeletions, paternally inherited X-linked recessive genetic variants, and de novo X-linked recessive genetic variants, maternally inherited X-linked variants in the fetus can be detected in methods using a maternal haplotype. In some embodiments, maternal genomic DNA is isolated from the pregnant mother, for example from leukocytes present in a buffy coat. At least one region of interest corresponding to the region of interest in the cell-free DNA is sequenced from the maternal genomic DNA. Optionally, the maternal genomic DNA is enriched at the corresponding region of interest. Also optionally, molecular barcodes are used with the maternal genomic DNA. The maternal haplotypes are then constructed, for example using molecular phasing technologies, using a sequence of a biological relative, or using statistical haplotype mapping.

An increase or decrease in the read frequency at a particular allele is computed relative to each haplotype, which indicates variance between the cell-free DNA and each maternal haplotype. This indicates which maternal haplotype is enriched in the cell-free DNA, and is thus attributable to the fetal genome.

Small Nucleotide Polymorphism Genetic Variant Detection

In some embodiments, provided herein is a method of detecting the presence or absence of a genetic variant in a region of interest in the genome of a fetus in a pregnant woman, wherein the fetal genetic variant is a de novo small nucleotide polymorphism genetic variant or a paternally-inherited small nucleotide polymorphism genetic variant. In some embodiments, the father's genome is sequenced to reveal whether the genetic variant is a paternally inherited genetic variant or a de novo genetic variant. That is, if the fetal genetic variant is not present in the father, and the described method indicates that the fetal genetic variant is distinguishable from the maternal genome, then the fetal genetic variant is a de novo variant. Accordingly, provided herein is a method of determining whether a fetal genetic variant is an inherited genetic variant or a de novo genetic variant.

Cell-free DNA can be extracted from plasma of a pregnant woman (i.e., maternal plasma). The plasma comprises cell-free DNA from the fetal genome and cell-free DNA from the maternal genome. A DNA library is then formed from the cell-free DNA and the region of interest is enriched, thereby forming a population of enriched DNA molecules that correspond to the region of interest. The enriched DNA molecules are then sequenced to produce a plurality of cell-free sequencing reads. In some embodiments, molecular barcodes are employed. In some embodiments, the molecular barcodes are used to distinguish single nucleotide polymorphisms variants from random mutations.

The plurality of cell-free sequencing reads comprises sequencing reads from the fetal region of interest and sequencing reads from the maternal region of interest. An increase or decrease in the read frequency at a particular allele is computed, which indicates variance between the fetal genome and the maternal genome. A variant call can be made on the basis of that variance. In some embodiments, the variance is above (in the case of an increase in read frequency) or below (in the case of a decrease in read frequency) a predetermined threshold to trigger a variant call. Variance between the fetal and maternal genome for a region of interest is generally due to either a paternally inherited chromosome or a de novo mutation.

In addition to the accurate detection of large copy number variants (such as aneuploidy), microdeletions, paternally inherited or de novo genetic variants, maternally inherited genetic variants in the fetus can be detected in methods using a maternal haplotype. In some embodiments, maternal genomic DNA is isolated from the pregnant mother, for example from leukocytes present in a buffy coat. At least one region of interest corresponding to the region of interest in the cell-free DNA is sequenced from the maternal genomic DNA. Optionally, the maternal genomic DNA is enriched at the corresponding region of interest. Also optionally, molecular barcodes are used with the maternal genomic DNA. The maternal haplotypes are then constructed, for example using molecular phasing technologies, using a sequence of a biological relative, or using statistical haplotype mapping.

An increase or decrease in the read frequency at a particular allele is computed relative to each haplotype, which indicates variance between the cell-free DNA and each maternal haplotype. This indicates which maternal haplotype is enriched in the cell-free DNA, and is thus attributable to the fetal genome and is a fetal genetic variant.

To determine whether a fetal genetic variant is a de novo genetic variant or a paternally inherited genetic variant, the region of interest in the paternal genome is sequenced (optionally following targeted enrichment of the region of interest). If the genetic variant is not present in the paternal genome, and it cannot be attributed to the maternal genome (either by sequencing the corresponding region of interest in the maternal genome or by using the methods described herein), then it is a de novo genetic variant. If the genetic variant is present in the paternal genome, and it cannot be attributed to the maternal genome (either by sequencing the corresponding region of interest in the maternal genome or by using the methods described herein), then it is substantially likely to be a paternally-inherited genetic variant.

Copy Number Variant (CNV) Detection

In some embodiments, provided herein is a method of detecting the presence or absence of a genetic variant in a region of interest in the genome of a fetus in a pregnant woman, wherein the fetal genetic variant is a de novo copy number variant (such as a copy number loss variant) or a paternally-inherited copy number variant (such as a copy number loss variant). In some embodiments, the father's genome is sequenced to reveal whether the copy number variant is a paternally inherited copy number variant or a de novo copy number variant. That is, if the fetal copy number variant is not present in the father, and the described method indicates that the fetal copy number variant is distinguishable from the maternal genome, then the fetal copy number variant is a de novo copy number variant. Accordingly, provided herein is a method of determining whether a fetal copy number variant is an inherited copy number variant or a de novo copy number variant.

Cell-free DNA can be extracted from plasma of a pregnant woman (i.e., maternal plasma). The plasma comprises cell-free DNA from the fetal genome and cell-free DNA from the maternal genome. A DNA library is then formed from the cell-free DNA and the region of interest is enriched, thereby forming a population of enriched DNA molecules that correspond to the region of interest. The enriched DNA molecules are then sequenced to produce a plurality of cell-free sequencing reads. In some embodiments, molecular barcodes are employed. In some embodiments, the molecular barcodes are used to distinguish single nucleotide polymorphisms variants from random mutations.

The plurality of cell-free sequencing reads comprises sequencing reads from the fetal region of interest and sequencing reads from the maternal region of interest. An increase or decrease in the read frequency at a particular allele is computed, which indicates variance between the fetal genome and the maternal genome. A copy number variant call can be made on the basis of that variance. In some embodiments, the variance is above (in the case of an increase in read frequency) or below (in the case of a decrease in read frequency) a predetermined threshold to trigger a variant call. Variance between the fetal and maternal genome for a region of interest is generally due to either a paternally inherited chromosome or a de novo mutation.

In addition to the accurate detection of large copy number variants (such as aneuploidy), microdeletions, paternally inherited or de novo genetic variants, maternally inherited genetic variants in the fetus can be detected in methods using a maternal haplotype. In some embodiments, maternal genomic DNA is isolated from the pregnant mother, for example from leukocytes present in a buffy coat. At least one region of interest corresponding to the region of interest in the cell-free DNA is sequenced from the maternal genomic DNA. Optionally, the maternal genomic DNA is enriched at the corresponding region of interest. Also optionally, molecular barcodes are used with the maternal genomic DNA. The maternal haplotypes are then constructed, for example using molecular phasing technologies, using a sequence of a biological relative, or using statistical haplotype mapping.

An increase or decrease in the read frequency at a particular allele is computed relative to each haplotype, which indicates variance between the cell-free DNA and each maternal haplotype. This indicates which maternal haplotype is enriched in the cell-free DNA, and is thus attributable to the fetal genome and is a fetal genetic variant.

Autosomal Recessive Variant Detection

In some embodiments, provided herein is a method of detecting the presence or absence of a genetic variant in a region of interest in the genome of a fetus in a pregnant woman, wherein the fetal genetic variant is an autosomal recessive fetal genetic variant. In some embodiments, the autosomal fetal genetic variant is a small nucleotide polymorphism. In some embodiments, the fetal genetic variant is a copy number variant, such as a copy number loss variant, or a microdeletion.

In some embodiments, cell-free DNA is extracted from the plasma of a pregnant woman. In some embodiments, maternal genomic DNA is also extracted, for example, from a maternal buffy coat. A DNA library comprising a plurality of DNA molecules can be prepared from the extracted cell-free DNA, which can include incorporation of oligonucleotides. The oligonucleotides can comprise, for example, one or more of site-specific sequences (i.e., for targeted enrichment), a molecular barcode, or a sequencing adapter. Optionally, in some embodiments, a maternal DNA library is prepared from maternal genomic DNA, which can also include the incorporation of oligonucleotides.

The DNA library (or DNA libraries if a maternal DNA library is included) is then analyzed at a predetermined region of interest. In some embodiments, the analysis comprises enriching DNA molecules in the DNA library for those DNA molecules which comprise the region of interest or a portion of the region of interest, for example by hybridization, followed by sequencing or digital PCR of the enriched DNA molecules. In some embodiments, the analysis comprises simultaneously enriching and sequencing the DNA molecules comprising the region of interest or a portion of the region of interest, for example by selectively sequencing DNA molecules.

In some embodiments, the sequenced DNA molecules are then aligned to generate "long reads" of the region of interest. Alternatively, the short sequencing reads can be queried for known genetic sequence variants (which would not require alignment of the sequencing reads).

In some embodiments, maternal haplotypes are constructed, for example using molecular phasing technologies, using a sequence of a biological relative, or using statistical haplotype mapping. An increase or decrease in the read frequency at a particular allele is computed relative to each haplotype, which indicates variance between the cell-free DNA and each maternal haplotype. This indicates which maternal haplotype is enriched in the cell-free DNA, and is thus attributable to the fetal genome and is a fetal genetic variant.

EXAMPLES

The examples below are intended to be purely exemplary of the invention and should therefore not be considered to limit the invention in any way. The following examples and detailed description are offered by way of illustration and not by way of limitation.

Example 1: De Novo Small Nucleotide Polymorphism Detection Assay Development

This example demonstrates the development of an assay for the detection of de novo (non-inherited) small nucleotide polymorphisms in the fetus, and can be used, for example, to determine DNA library concentrations for any particular region of interest.

To establish the sensitivity of a de novo detection assay, a dilution series of cell-line-derived or plasma-derived DNA, with at least one known mutation, in a background of plasma-derived DNA not carrying that mutation is prepared. A DNA library, with incorporated molecular barcodes is prepared from each sample of the dilution series. Subsequently, the DNA library samples are enriched for a region of interest surrounding the known mutation. Optionally, targeting enrichment can be accomplished during the step of creating a DNA library if a PCR-based target enrichment protocol is used to prepare the DNA library. Next, the enriched library samples are sequenced at a depth predicted to be sufficient to detect the variant of interest at each dilution level (according to a binomial sensitivity curve). Small nucleotide polymorphism calling is used to determine small nucleotide polymorphism variants. The sensitivity of the de novo detection assay is characterized as a function of dilution fraction, sequencing depth (by computational sub-sampling), and sequencing error rate and duplication rate (by including or excluding molecular barcodes from analysis).

Example 2: Paternally Inherited and De Novo Small Nucleotide Polymorphism Detection This example demonstrates the detection of paternally inherited and de novo small nucleotide polymorphisms in the fetus from cell-free DNA obtained from the mother. Paternally inherited small nucleotide polymorphisms are indistinguishable in the plasma from de novo small nucleotide polymorphisms, as neither will appear in the background maternal DNA, without further analysis (such as paternal genome sequencing or paternal haplotype construction)

One or more samples of cell-free DNA are obtained from the blood plasma of a pregnant woman. A DNA library is prepared from the cell-free DNA sample. Optionally, based on the sensitivity of the assay, as determined by, for example, the method discussed in Example 1, molecular barcodes may be incorporated if judged necessary for assay performance at desired fetal fractions. Next, the sample is enriched for a region of interest which is expected to contain one or more loci at which the father carries a different small nucleotide polymorphism allele than the mother. The enriched libraries are then sequenced and analyzed to call putative paternal variants. The presence of the detected variants are optionally validated by: (a) sequencing the maternal genome at the same sites to verify that the variants are not present in the mother (including as low-level mosaicism); (b) sequencing the paternal genome at the same sites to verify that the variants are in fact present in the father; and/or (c) sequencing the child's genome (for example, either from an amniotic fluid/chorionic villus sample in the prenatal context, or from a sample from the child postnatally) to verify the presence of the variant in the child.

If the sequence analysis of the maternal and paternal genome is completed, the detected small nucleotide polymorphism can be further classified as either a de novo small nucleotide polymorphism or a paternally inherited small nucleotide polymorphism. If the presence of the variant in the child is confirmed by sequencing the child genome (see (c) in above paragraph; e.g., either from an amniotic fluid/chorionic villus sample in the prenatal context, or from a sample from the child postnatally), and the variant is not present in the maternal genome, then comparison to the paternal genome will determine the nature of the variant. Specifically, a variant that is present in the paternal genome is likely to be inherited and a variant that is absent in the paternal genome can be assumed to have arisen de novo.

Example 3: De Novo Deletion Detection Assay Development

This example demonstrates the development of an assay for the detection of de novo deletion in the fetus, and can be used, for example to determine DNA library concentrations for any particular region of interest.

To establish the sensitivity of a de novo deletion detection assay, a dilution series of a cell-line or plasma sample known to be positive for a heterozygous or hemizygous copy number loss variant is prepared. A DNA library, with incorporated molecular barcodes is prepared from each sample of the dilution series. Subsequently, the DNA library samples are enriched for a region of interest surrounding the known mutation. Optionally, targeting enrichment can be accomplished during the step of creating a DNA library if a PCR-based target enrichment protocol is used to prepare the DNA library. Next, the enriched library samples are sequenced at a depth predicted to be sufficient to detect the copy number variation of interest at each dilution level (according to a binomial sensitivity curve). Copy number calling is used to determine copy number variation. The sensitivity of the de novo deletion detection assay is characterized as a function of dilution fraction, sequencing depth (by computational subsampling), and sequencing error rate and duplication rate (by including or excluding molecular barcodes from analysis).

Example 4: Paternally Inherited and De Novo Deletion Detection Assay Development This example demonstrates the detection of paternally inherited and de novo deletions in the fetus from cell-free DNA obtained from the mother. In the mother's plasma, paternally inherited deletions are indistinguishable from de novo deletions, as neither will appear in the background maternal DNA.

A sample from a cell-line or plasma sample known to be positive for a heterozygous or hemizygous copy number loss variant is prepared. For example, a suitable sample may originate from a female fetus from a father affected by deletional Duchenne or Becker muscular dystrophy or a male fetus found to be carrying deletional Duchenne or Becker muscular dystrophy by amniocentesis or chorionic callus sampling, in the absence of such variant in the mother. A DNA library is prepared from the sample. Optionally, based on the sensitivity of the assay, as determined by, for example, the method discussed in Example 3, molecular barcodes may be incorporated if judged necessary for assay performance at desired fetal fractions. Next, the sample is enriched for a region of interest which is expected to contain one or more loci at which the father carries a different allele than the mother. The enriched libraries are then sequenced and analyzed to call putative paternal copy number variant. The presence of the detected variants are optionally validated by: (a) sequencing the maternal genome at the same sites to verify that the variants are not present in the mother (including as low-level mosaicism); (b) sequencing the paternal genome at the same sites to verify that the variants are in fact present in the father; and/or (c) sequencing the child's genome (for example, either from an amniotic fluid/chorionic villus sample in the prenatal context, or from a sample from the child postnatally) to verify the presence of the variant in the child.

If the sequence analysis of the maternal and paternal genome is completed, the detected deletion can be further classified as either a de novo deletion or a paternally inherited deletion. If the presence of the deletion in the child is confirmed by sequencing the child genome (see (c) in above paragraph; e.g., either from an amniotic fluid/chorionic villus sample in the prenatal context, or from a sample from the child postnatally), and the deletion is not present in the maternal genome, then comparison to the paternal genome will determine the nature of the deletion. Specifically, a deletion that is present in the paternal genome is likely to be inherited and a deletion that is absent in the paternal genome can be assumed to have arisen de novo.

Example 4: Clinical Trial Evaluating Non-Invasive Prenatal Testing

This example demonstrates a clinical trial for determining the presence of fetal de novo or inherited genetic conditions using non-invasive prenatal testing of the mother.

Pregnant woman at greater than 10-weeks gestational age are enrolled in a clinical trial to determine the presence of fetal de novo or inherited genetic conditions. Contemplated genetic conditions to be tested for include, but are not limited to, de novo variants arising in FGFR3 causing skeletal dysplasias, de novo small nucleotide polymorphisms, additions, and deletions in the dystrophin gene (DMD) causing Duchenne or Becker muscular dystrophies, de novo or maternally inherited variants in DMD causing Duchenne or Becker muscular dystrophy, compound heterozygosity of pathogenic alleles in the cystic fibrosis transmembrane conductance regulator gene (CFTR) causing cystic fibrosis when both parents are carriers for distinct pathogenic alleles in CFTR, and homozygosity for the F508del variant in CFTR when both parents are carriers of this variant.

Two 10 mL whole blood samples are obtained from the mother in Streck Cell-Free DNA BCT collection tubes. The samples are shipped at ambient temperature using next-day shipping to a central receiving laboratory performing the testing. The receiving laboratory will assess each sample to ensure physical integrity of the sample, proper collection procedure and volume, and consistency with ordering guidelines.

The blood sample is processed to extract cell-free DNA ("cfDNA") from plasma. Optionally, the maternal genomic DNA ("gDNA") from Buffy coat fraction is extracted. A DNA library from cfDNA is prepared by incorporation of sample-specific oligonucleotide sequence (sample barcode), unique molecular identifier oligonucleotide (molecular barcode), and instrument-specific sequencing oligonucleotide (sequencing adapter). The incorporation of the sample barcode, molecular barcode, and sequence adapter can be performed in one step through the construction of an appropriate combinatorial oligonucleotide set. Alternatively, instead of preparing a DNA library, the cfDNA sample is analyzed by direct digital PCR.

If a gDNA sample was acquired, a DNA library from gDNA is prepared by incorporation of sample-specific oligonucleotide sequence (sample barcode), unique molecular identifier oligonucleotide (molecular barcode), and instrument-specific sequencing oligonucleotide (sequencing adapter). Optionally, the molecular barcode is excluded. The incorporation of the sample barcode, molecular barcode, and sequence adapter can be performed in one step through the construction of an appropriate combinatorial oligonucleotide set. Optionally, a second set of molecular barcodes is introduced into the gDNA in physical proximity of the first molecular barcode to enable later reconstruction of long-distance relationships from short-read data.

The cfDNA and gDNA sequence libraries are enriched for DNA containing regions of interest for testing. The enriched sequence libraries are then sequenced on a next-generation sequencer using, for example, sequencing-by-synthesis chemistry with reversible terminators. The sequence reads are aligned to a human genome reference. Alternatively, analysis is performed without alignment, for example, by building a database of short nucleotide sequences known to be associated with disease carrier states and querying this database without conventional sequence alignment or the use of a reference genome. Optionally, the sequences are phased by analyzing the data using the physically-proximal molecular barcodes to reconstruct the phase relationship of (disease-causing or non-disease-causing) variants in the maternal genome in the region of interest.

Bioinformatic analysis of the aligned sequence reads is conducted to detect the presence or absence of a desired variant of interest. Depending on the intended test, bioinformatics analysis will detect small nucleotide polymorphisms or estimation of the fetal copy number in a targeted region. If the maternal genome is phased, then the analysis requires the incorporation of phased maternal genome data to extend the size of a region whose depth can be accurately called.

Based on the results of analysis, a report is generated and issued to the prescribing physician and patient indicating the likely presence or absence of disease-causing variants in the fetus in the designated region of interest. If a positive test result is indicated, the prescribing physician may choose to positively confirm this result by prenatal diagnostic testing, for example, amniocentesis or chorionic villus sampling.

Example 5: Determining X-linked Recessive Traits without Phasing

This example demonstrates an assay for determining the presence of X-linked recessive traits without phasing using non-invasive prenatal testing of the mother.

A whole blood sample from the pregnant mother is obtained. The cfDNA is extracted from the maternal plasma. The cfDNA is sequenced at one or more sites using a target enrichment strategy. The enrichment or depletion of sequencing reads is determined. Paternally inherited or de novo small nucleotide polymorphisms and additions or deletions are determined as discussed herein. A report is generated detailing the presence (or absence) of fetal copy number at relevant targeted genes and/or the presence of fetal small nucleotide polymorphisms and additions or deletions in relevant targeted genes.

Example 6: Determining X-linked Recessive Traits with Phasing

This example demonstrates an assay for determining the presence of X-linked recessive traits with phasing using non-invasive prenatal testing of the mother.

A whole blood sample from the pregnant mother is obtained. The cfDNA is extracted from the maternal plasma. The maternal genomic DNA (gDNA) is extracted from the maternal Buffy coat. The cfDNA is sequenced at one or more sites using a target enrichment strategy. The gDNA is phased by using, for example, 10× or Illumina synthetic long read molecular phasing technology, trio or other relatives' genomic information, or statistical haplotype information. The enrichment or depletion of sequencing reads is determined from each haplotype. Paternally inherited or de novo small nucleotide polymorphisms and additions or deletions are determined as discussed herein. If the mother is a carrier for a deleterious allele, the haplotype information is used to determine which maternal haplotype is enriched in the cfDNA by combing counts across multiple phased small nucleotide polymorphisms and addition or deletion sites. A report is generated detailing the presence (or absence) of fetal copy number at relevant targeted genes and/or the presence of fetal small nucleotide polymorphisms and additions or deletions in relevant targeted genes.

Example 7: De Novo Autosomal Dominant Trait Detection

This example demonstrates an assay for determining the presence of de novo autosomal dominant traits using non-invasive prenatal testing of the mother.

A whole blood sample from the pregnant mother is obtained. The cfDNA is extracted from the maternal plasma. The cfDNA is sequenced at one or more sites using a target enrichment strategy. The enrichment or depletion of sequencing reads is determined. De novo small nucleotide polymorphisms and additions or deletions are determined as discussed herein. A report is generated detailing the presence (or absence) of fetal copy number at relevant targeted genes and/or the presence of fetal small nucleotide polymorphisms and additions or deletions in relevant targeted genes.

The invention claimed is:
1. A method of detecting the presence or absence of a genetic variant in a region of interest in the genome of a fetus in a pregnant woman, comprising:
    (a) extracting circulating cell-free DNA from a plasma sample of the pregnant woman;

(b) extracting maternal genomic DNA (gDNA) from a sample of the pregnant woman;
(c) preparing a first DNA library from said cell-free DNA, the first DNA library comprising a first population of DNA molecules comprising covalently linked molecular barcodes and that is enriched for a region of interest in said cell-free DNA, wherein the sequence of each molecular barcode differs from the sequence of every other molecular barcode;
(d) preparing a second DNA library from said gDNA, the second DNA library comprising a second population of DNA molecules comprising first and second covalently linked molecular barcodes and that is enriched for a region of interest in said gDNA, wherein the sequence of each molecular barcode differs from the sequence of every other molecular barcode;
(e) sequencing the region of interest in the first population of DNA molecules from said first DNA library to produce a plurality of cell-free DNA sequencing reads;
(f) sequencing a region of interest in the second population of DNA molecules from said second DNA library that corresponds to the region of interest in the cell-free DNA to produce a plurality of gDNA sequencing reads by performing long read-length sequencing technologies, wherein said long read-length sequencing technologies produces sequence reads greater than 500 bases, and constructing a maternal haplotype by phasing genetic variants present only in the gDNA sequencing reads; and
(g) detecting the presence or absence of a fetal genetic variant based on the cell-free DNA sequencing reads and the maternal haplotype,
wherein the fetal genetic variant is a single-nucleotide variant, a multi-nucleotide variant, an indel variant of 100 bp or less, or a copy number loss variant within a region of interest of 50,000 bp or fewer.

2. A method of detecting the presence or absence of a genetic variant in a region of interest in the genome of a fetus in a pregnant woman, comprising:
(a) extracting circulating cell-free DNA from a plasma sample of the pregnant woman;
(b) extracting maternal genomic DNA (gDNA) from a sample of the pregnant woman;
(c) preparing a first DNA library from said cell-free DNA, wherein the first DNA library comprises a first plurality of DNA molecules comprising molecular barcodes, wherein the sequence of each molecular barcode differs from the sequence of every other molecular barcode;
(d) preparing a second DNA library from said gDNA, wherein the second DNA library comprises a second plurality of DNA molecules comprising a first and a second set of molecular barcodes, wherein the sequence of each molecular barcode differs from the sequence of every other molecular barcode;
(e) sequencing the region of interest in the first plurality of DNA molecules to produce a plurality of cell-free DNA sequencing reads; and
(f) sequencing a region of interest in the second plurality of DNA molecules that corresponds to the region of interest in the first plurality of DNA molecules to produce a plurality of gDNA sequencing reads by performing long read-length sequencing technologies, wherein said long read-length sequencing technologies produces sequence reads greater than 500 bases, and constructing a maternal haplotype by phasing genetic variants present only in the gDNA sequencing reads; and
(g) detecting the presence or absence of a fetal genetic variant based on the cell-free DNA sequencing reads and the maternal haplotype,
wherein the fetal genetic variant is a single-nucleotide variant, a multi-nucleotide variant, an indel variant of 100 bp or less, or a copy number loss variant within a region of interest of 50,000 bp or fewer.

3. A method of detecting the presence or absence of a genetic variant in a region of interest in the genome of a fetus in a pregnant woman, comprising:
(a) obtaining a first population of DNA molecules from a first DNA library comprising a first plurality of DNA molecules comprising molecular barcodes, wherein the first DNA library is prepared from circulating cell-free DNA extracted from a plasma sample of the pregnant woman, wherein the first population of DNA molecules is enriched for a region of interest in said cell-free DNA, wherein the molecular barcodes are incorporated into the first plurality of DNA molecules prior to enrichment, and wherein the sequence of each molecular barcode differs from the sequence of every other molecular barcode;
(b) obtaining a second population of DNA molecules from a second DNA library comprising a second plurality of DNA molecules comprising a first and a second set of molecular barcodes, wherein the second DNA library is prepared from gDNA extracted from a sample of the pregnant woman, wherein the second population of DNA molecules is enriched for a region of interest in said gDNA, wherein the first and second sets of molecular barcodes are incorporated into the second plurality of DNA molecules prior to enrichment, and wherein the sequence of each molecular barcode differs from the sequence of every other molecular barcode;
(c) sequencing the region of interest in the first population of DNA molecules to produce a plurality of cell-free DNA sequencing reads; and
(d) sequencing a region of interest in the second population of DNA molecules that corresponds to the region of interest in the cell-free DNA to produce a plurality of maternal sequencing reads by performing long read-length sequencing technologies, wherein said long read-length sequencing technologies produces sequence reads greater than 500 bases, and constructing a maternal haplotype by phasing genetic variants present only in the maternal sequencing reads; and
(e) detecting the presence or absence of a fetal genetic variant based on the cell-free DNA sequencing reads and the maternal haplotype,
wherein the fetal genetic variant is a single-nucleotide variant, a multi-nucleotide variant, an indel variant of 100 bp or less, or a copy number loss variant within a region of interest of 50,000 bp or fewer.

4. A method of detecting the presence or absence of a genetic variant in a region of interest in the genome of a fetus in a pregnant woman, comprising:
(a) extracting circulating cell-free DNA from a plasma sample of the pregnant woman;
(b) extracting gDNA from a sample of the pregnant woman;
(c) preparing a first DNA library from said cell-free DNA, wherein the first DNA library comprises a first plurality of DNA molecules comprising covalently linked molecular barcodes, wherein a portion of the first plurality of DNA molecules is enriched for a region of interest in said cell-free DNA, wherein the molecular barcodes are incorporated into the first plurality of DNA molecules prior to enrichment, and wherein the sequence of each molecular barcode differs from the sequence of every other molecular barcode;

(d) preparing a second DNA library from said gDNA, wherein the second DNA library comprises a second plurality of DNA molecules comprising a first and a second set of covalently linked molecular barcodes, wherein a portion of the second plurality of DNA molecules is enriched for a region of interest that corresponds to the region of interest in said cell-free DNA, wherein the first and second sets of molecular barcodes are incorporated into the second plurality of DNA molecules prior to enrichment, and wherein the sequence of each molecular barcode differs from the sequence of every other molecular barcode;

(e) sequencing the region of interest in the portion of the first DNA library to produce a plurality of cell-free DNA sequencing reads; and (f) sequencing the region of interest in the second DNA library that corresponds to the region of interest in the cell-free DNA to produce a plurality of maternal sequencing reads by performing long read-length sequencing technologies, wherein said long read-length sequencing technologies produces sequence reads greater than 500 bases, and constructing a maternal haplotype by phasing genetic variants present only in the maternal sequencing reads; and (g) detecting the presence or absence of a fetal genetic variant based on the cell-free DNA sequencing reads and the maternal haplotype, wherein the fetal genetic variant is a single-nucleotide variant, a multi-nucleotide variant, an indel variant of 100 bp or less, or a copy number loss variant within a region of interest of 50,000 bp or fewer.

5. The method of claim 1, wherein preparation of the population of DNA molecules that is enriched for the region of interest carried out by PCR amplification.

6. The method of claim 1, wherein preparation of the population of DNA molecules that is enriched for the region of interest is carried out by hybridization.

7. The method of claim 1, wherein the method detects the presence of the fetal genetic variant.

8. The method of claim 1, wherein the method detects the absence of the fetal genetic variant.

9. The method of claim 1, wherein the region of interest in the genome of the pregnant woman that corresponds to the region of interest in the cell-free DNA is sequenced from DNA present in a maternal buffy coat.

10. The method of claim 1, wherein detecting the presence or absence of the fetal genetic variant comprises:
computing a maternal allele frequency for the maternal sequencing reads;
computing a cell-free DNA allele frequency for the cell-free DNA sequencing reads; and
comparing the maternal allele frequency to the cell-free DNA allele frequency.

11. The method of claim 1, wherein the fetal genetic variant is a single-nucleotide variant, and wherein detecting the presence or absence of the fetal genetic variant comprises using a molecular barcode to distinguish the single-nucleotide variant from random or systematic errors.

12. The method of claim 1, wherein the fetal genetic variant is a DNA deletion variant.

13. The method of claim 1, wherein the fetal genetic variant is a de novo variant.

14. The method of claim 1, wherein the fetal genetic variant is an inherited variant.

15. The method of claim 14, wherein the fetal genetic variant is maternally inherited.

16. The method of claim 14, wherein the fetal genetic variant is paternally inherited.

17. The method of claim 1, wherein the fetal genetic variant is an autosomal dominant variant.

18. The method of claim 1, wherein the fetal genetic variant is an autosomal recessive variant.

19. The method of claim 18, wherein the region of interest comprises a CFTR gene or a fragment thereof or a FGFR3 gene or a fragment thereof.

20. The method of claim 1, wherein the fetal genetic variant is an X-linked recessive variant.

21. The method of claim 20, wherein the region of interest is the Duchenne muscular dystrophy (DMD) gene or a fragment thereof.

22. The method of claim 1, wherein said detecting comprises detection of a plurality of genetic variants.

23. The method of claim 22, wherein the plurality of genetic variants are in the same region of interest.

24. The method of claim 23, wherein the plurality of genetic variants are in different regions of interest.

25. The method of claim 1, wherein the gestational age of the fetus is about 10 weeks or more.

26. The method of claim 2, wherein the fetal genetic variant is an X-linked recessive genetic variant.

27. The method of claim 3, wherein the fetal genetic variant is an X-linked recessive genetic variant.

28. The method of claim 4, wherein the fetal genetic variant is an X-linked recessive genetic variant.

29. The method of claim 1, wherein long read-length sequencing technologies comprises single molecule sequencing.

30. A method of preparing a sample for detection of the presence or absence of a genetic variant in a region of interest in the genome of a fetus in a pregnant woman, comprising:

(a) extracting circulating cell-free DNA from a plasma sample of the pregnant woman;

(b) extracting maternal genomic DNA (gDNA) from a sample of the pregnant woman;

(c) preparing a first DNA library from said cell-free DNA, wherein the first DNA library comprises a plurality of DNA molecules comprising molecular barcodes, wherein the sequence of each molecular barcode differs from the sequence of every other molecular barcode;

(d) preparing a second DNA library from said gDNA, wherein the second DNA library comprises a plurality of DNA molecules comprising a first set and a second set of molecular barcodes, wherein the sequence of each molecular barcode differs from the sequence of every other molecular barcode;

(e) sequencing the region of interest in the portion of the first DNA library to produce a plurality of cell-free DNA sequencing reads;

(f) sequencing a region of interest in the second population of DNA molecules from said second DNA library that corresponds to the region of interest in the cell-free DNA to produce a plurality of gDNA sequencing reads by performing long read-length sequencing technologies, wherein said long read-length sequencing technologies produces sequence reads greater than 500 bases;

(g) constructing a maternal haplotype by phasing genetic variants present only in the gDNA sequencing reads; and (h) detecting the presence or absence of a fetal genetic variant based on the cell-free DNA sequencing reads and the maternal haplotype, wherein the fetal genetic variant is a single-nucleotide variant, a multi-nucleotide variant, an indel variant of 100 bp or less, or a copy number loss variant within a region of interest of 50,000 bp or fewer.

31. The method of claim 30, wherein the gDNA sequencing reads are phased using the first and second sets of molecular barcodes to reconstruct the phase relationship of variants in the gDNA in the region of interest.

* * * * *